(12) United States Patent
Pruitt et al.

(10) Patent No.: US 7,780,635 B2
(45) Date of Patent: Aug. 24, 2010

(54) APPARATUS AND METHODS FOR DELIVERING FLUID AND MATERIAL TO A SUBJECT

(75) Inventors: Terrell Pruitt, Lawrenceville, GA (US); Stephen A. Cochran, Tucker, GA (US); Bryan Marshall, Atlanta, GA (US); Yandong Su, Atlanta, GA (US); Kurt Stricker Stenn, Princeton, NJ (US); Kenneth Justin Washenik, Beverly Hills, CA (US); John DePiano, Burlington, MA (US); Gary F. Prokop, Wheaton, IL (US); Martin Rathgeber, Chicago, IL (US)

(73) Assignee: Aderans Research Institute, Inc., Marietta, GA (US)

( * ) Notice: Subject to any disclaimer, the term of this patent is extended or adjusted under 35 U.S.C. 154(b) by 855 days.

(21) Appl. No.: 11/672,675

(22) Filed: Feb. 8, 2007

(65) Prior Publication Data
US 2007/0233038 A1 Oct. 4, 2007

Related U.S. Application Data

(60) Provisional application No. 60/771,915, filed on Feb. 9, 2006, provisional application No. 60/791,489, filed on Apr. 12, 2006, provisional application No. 60/803,248, filed on May 26, 2006.

(51) Int. Cl.
*A61M 31/00* (2006.01)
*A61M 5/00* (2006.01)
(52) U.S. Cl. .................. 604/187; 604/522; 604/506; 604/188; 604/224
(58) Field of Classification Search ............. 604/506, 604/95.01, 131, 155–156, 159, 184, 187, 604/188, 193–197, 208, 211, 218, 224, 232, 604/233–235, 522
See application file for complete search history.

(56) References Cited

U.S. PATENT DOCUMENTS 2,472,116 A * 6/1949 Maynes .................. 604/136

(Continued)

FOREIGN PATENT DOCUMENTS

EP 971679 6/2002

(Continued)

OTHER PUBLICATIONS

U.S. Appl. No. 11/811,744, filed Jun. 12, 2007, Zheng et al.
Atala A. (2004) Tissue engineering and regenerative medicine: concepts for clinical application. Rejuvenation Res 7:15-31.
Atlas of Anatomy Barron's Educational Series, Inc., 1997, p. 72.

(Continued)

*Primary Examiner*—Nicholas D Lucchesi
*Assistant Examiner*—Quynh-Nhu H Vu
(74) *Attorney, Agent, or Firm*—Pabst Patent Group LLP

(57) ABSTRACT

The present invention provides fluid and material delivery methods and devices for practicing the methods. The invention provides a method of delivering cellular material comprising injecting the cellular material into a subject such that the injected cells retain their inherent morphologic characteristics upon injection. The method comprises the steps of aspirating the cellular material into a fluid delivery device which incorporates a syringe arrangement. The cellular material is aspirated into the main body of the syringe until the desired amount of a material has filled the syringe body. The needle of the fluid delivery device is then inserted into the skin of a subject at an angle about parallel to the skin until a desired depth has been reached. The cellular material is then injected in the subject until the desired volume of material has been injected. The needle of the device is then rotated approximately 45 to 90 degrees and the needle is removed from the injection site.

31 Claims, 18 Drawing Sheets

U.S. PATENT DOCUMENTS

| | | | |
|---|---|---|---|
| 3,596,292 | A | 8/1971 | Erb et al. |
| 4,458,678 | A | 7/1984 | Yannas et al. |
| 4,659,327 | A * | 4/1987 | Bennett et al. ............... 604/135 |
| 5,376,542 | A | 12/1994 | Schlegal |
| 5,423,778 | A | 6/1995 | Eriksson et al. |
| 5,505,704 | A * | 4/1996 | Pawelka et al. .............. 604/191 |
| 5,611,811 | A | 3/1997 | Goldberg |
| 5,697,901 | A | 12/1997 | Eriksson |
| 5,817,120 | A | 10/1998 | Rassman |
| 5,957,896 | A * | 9/1999 | Bendek et al. .............. 604/207 |
| 5,989,279 | A | 11/1999 | Rassman |
| 5,993,374 | A | 11/1999 | Kick |
| 5,997,468 | A | 12/1999 | Wolff et al. |
| 6,027,744 | A | 2/2000 | Vacanti et al. |
| 6,062,753 | A | 5/2000 | Hadtke et al. |
| 6,387,077 | B1 * | 5/2002 | Klibanov et al. ............ 604/181 |
| 6,474,344 | B2 | 11/2002 | Yamada |
| 6,569,143 | B2 | 5/2003 | Alchas et al. |
| 6,660,301 | B1 | 12/2003 | Vogel et al. |
| 6,793,646 | B1 * | 9/2004 | Giambattista et al. ......... 604/90 |
| 6,884,427 | B1 | 4/2005 | Barrows |
| 6,890,319 | B1 | 5/2005 | Crocker |
| 7,198,641 | B2 | 4/2007 | Barrows |
| 7,534,222 | B2 * | 5/2009 | Sugita et al. .................. 604/82 |
| 2002/0172705 | A1 | 11/2002 | Murphy et al. |
| 2002/0193740 | A1 | 12/2002 | Alachas et al. |
| 2003/0009113 | A1 | 1/2003 | Olson |
| 2003/0147831 | A1 | 8/2003 | Marko |
| 2003/0161815 | A1 | 8/2003 | Wolowacz et al. |
| 2003/0198646 | A1 | 10/2003 | Stenn |
| 2003/0211083 | A1 | 11/2003 | Vogel et al. |
| 2003/0235813 | A1 | 12/2003 | Luyten et al. |
| 2004/0068284 | A1 | 4/2004 | Barrows |
| 2004/0096514 | A1 | 5/2004 | Vogel |
| 2004/0220589 | A1 | 11/2004 | Feller |
| 2005/0089512 | A1 | 4/2005 | Schlotmann et al. |
| 2005/0147652 | A1 | 7/2005 | Atkins et al. |
| 2005/0214344 | A1 | 9/2005 | Barrows |
| 2005/0233450 | A1 | 10/2005 | Goetinck et al. |
| 2006/0057126 | A1 | 3/2006 | Tankovich |
| 2006/0062770 | A1 | 3/2006 | Zheng et al. |
| 2006/0206057 | A1 * | 9/2006 | DeRuntz et al. ............. 604/224 |
| 2007/0092496 | A1 | 4/2007 | Zheng et al. |
| 2007/0122387 | A1 | 5/2007 | Cochran et al. |
| 2007/0148138 | A1 | 6/2007 | Barrows et al. |
| 2007/0191784 | A1 * | 8/2007 | Jacobs et al. ................ 604/224 |

FOREIGN PATENT DOCUMENTS

| | | |
|---|---|---|
| EP | 0845963 | 9/2003 |
| EP | 1702632 | 9/2006 |
| JP | 2001302520 | 10/2001 |
| JP | 2003235990 | 8/2003 |
| WO | WO 99/01034 | 1/1999 |
| WO | WO 00/09184 | 2/2000 |
| WO | WO 00/45736 | 10/2000 |
| WO | WO 01/66472 | 9/2001 |
| WO | WO 01/70132 | 9/2001 |
| WO | WO 01/70289 | 9/2001 |
| WO | WO 01/70290 | 9/2001 |
| WO | WO 01/70291 | 9/2001 |
| WO | WO 02/060396 | 8/2002 |
| WO | WO 02/083216 | 10/2002 |
| WO | WO 03/068248 | 8/2003 |
| WO | WO 03/088935 | 10/2003 |
| WO | WO 2005/018731 | 3/2005 |
| WO | WO 2005/053763 | 6/2005 |
| WO | WO 2005/097221 | 10/2005 |
| WO | WO 2006/020958 | 2/2006 |
| WO | WO 2006/057542 | 6/2006 |
| WO | WO 2007/047707 | 4/2007 |
| WO | WO 2007/062386 | 5/2007 |
| WO | WO 2007/062387 | 5/2007 |
| WO | WO 2007/092929 | 8/2007 |

OTHER PUBLICATIONS

Barrows TH, Cochran SA, Griffin EI and Solomon AR, "Tissue Engineered Human Hair: Preliminary Clinical Results" TE2002: International Workshop on Tissue Engineering, St. Gallen, Switzerland (Feb. 2002).

Castex-Rizzi et al., "Implication of VEGF,steroid hormones and neuropeptides in hair follicle cell responses," Ann. Dermatol. Venereol. (2002) 129(5):783-786.

Cotsarelis G, Sun TT, Lavker RM. (1990) "Label-retaining cells reside in the bulge area of pilosebaceous unit. Implications for follicular stem cells, hair cycle and skin carcinogenesis," Cell 61:1329-1337.

Gho et al., "Hair transplantation of plucked hair biopsies," Dermatol. Surg. (2001) 27(10):913.

Gho et al. To Multiply or Not to Multiply, That is the Question . . . , Dr. Coen Gho presentation at the International Society of Hair Restoration Surgeons 2003 New York City Conference, Oct. 19, 2003 (Abstract).

Horne et al., "Restoration of hair growth by surgical implantation of follicular dermal sheath," Development (1992) 116(3):563-571 Abstract.

Horne, Kenneth A, et al. "Whisker growth induced by implantation of cultured vibrissa dermal papilla cells in the adult rat" J Embryol Exp Morphol. Sep. 1986;97:111-24.

Inamatsu et al., "Establishment of rat dermal papilla cell lines that sustain the potency to induce hair follicles from afollicular skin" J Invest Dermatol. Nov. 1998;111(5):767-75.

Jahoda and Reynolds (2001) "Hair follicle dermal sheath cells: unsung participants in wound healing" Lancet 358:1445-1448.

Jahoda CA, "Induction of follicle formation and hair growth by vibrissa dermal papillae implanted into rat ear wounds: vibrissa-type fibres are specified" Development. Aug. 1992;115(4):1103-9.

Jahoda Cab, et al. (1993) "Induction of Hair Growth in Ear Wounds by Cultured Dermal Papilla Cells" J Invest Dermatol 101(4):584-590.

Jahoda Cab, et al., (1996) " Human Hair follicle regeneration following amputation and grafting into the nude mouse" J Invest Dermatol, 107(6):804-807.

Jahoda Cab, et al., "Induction of hair growth by implantation of cultured dermal papilla cells" Nature. Oct. 11-17, 1984;311(5986):560-2.

Jahoda, et al., "Trans-species hair growth induction by human hair follicle dermal papillae," Exp. Dermatol. (2001) 10:229-237.

Layer, P.G. et al., "Of layers and spheres: the reaggregate approach in tissue engineering," Trends Neurosci. (2002) 25:131-134.

Lee, K.H., "Tissue-engineered human living skin substitutes: development and clinical application," Yonsei Med. J. (2000) 41(6):774-779.

Lichti et al., "In vivo regulation of murine hair growth: insights from grafting defined cell populations onto nude mice" J Invest Dermatol. Jul. 1993;101(1 Suppl):124S-129S.

Lichti, AB, et al., "Hair follicle development and hair growth from defined cell populations granted onto nude mice," J Invest Dermat (1995) 104(5):43S-44S.

Magerl, M. et al., "Simple and rapid method to isolate and culture follicular papillae from human hair follicles," Exp. Dermatol. (2002) 11:381-385.

Matsuzaki et al., "The upper dermal sheath has a potential to regenerate the hair in the rat follicular epidermis," Differentiation (1996) 60(5):287-297 Abstract.

Mayorov, V.I. et al., "B2 elements present in the human genome," Mamm. Genome (2000) 11:177-179.

McElwee et al., "Cultured Peribulbar Dermal Sheath Cells Can Induce Hair Follicle Development and Contribute to the Dermal Sheath and Dermal Papilla" 2003 J. Invest Dermatol 121:1267-1275.

Michel et al., "Characterization of a new tissue-engineered human skin equivalent with hair," In Vitro Cell Dev Biol. Anim. (1999) 35(6):318-326.

Price, V.H., "Treatment of Hair Loss," N Eng J Med (1999) 341:964-973.

Rassman, W.R. et al., "Rapid fire hair implanter carousel," Dermatologic Surgery (1998) 24:623-627.

Remmler D, et al., "Use of injectable cultured human fibroblasts for percutaneous tissue implantation," Arch Otolaryngol Head Neck Surg (1989) 115:837-844.

Stenn et al., "Bioengineering the hair follicle: fringe benefits of stem cell technology," Curr. Opin. in Biotech. (2005) 16:1-5.

Stenn, et al., "Hair follicle growth controls," Dermatol Clinics (1996) 14:543-558.

Stenn, K. et al., "Growth of the Hair Follicle: A Cycling and Regenerating Biological System," The Molecular Basis of Epithelial Appendage Morphogenesis, ed. C-M Chuong, Landes Publ. Austin TX (1998) 111-130.

Stenn, K.S. et al., "Bioengineering the hair follicle: fringe benefits of stem cell technology," Curr. Opin. Biotech. (2005) 16(5):493-497.

Worst, P.K.M. et al., "Reformation of organized epidermal structure by transplantation of suspensions and cultures of epidermal and dermal cells," Cell Tiss. Res. (1982) 225(1):65-77.

Yang et al., "Cell sheet engineering: recreating tissue without biodegradable scaffolds," Biomaterials (2005) 26(33):6415-6422.

* cited by examiner

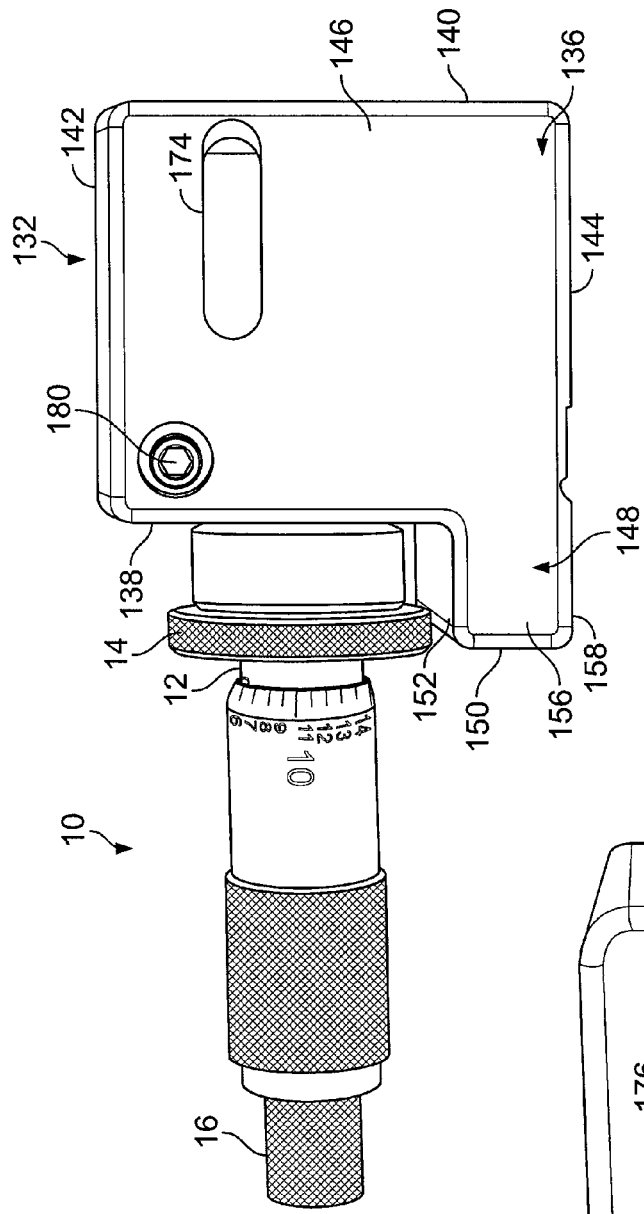
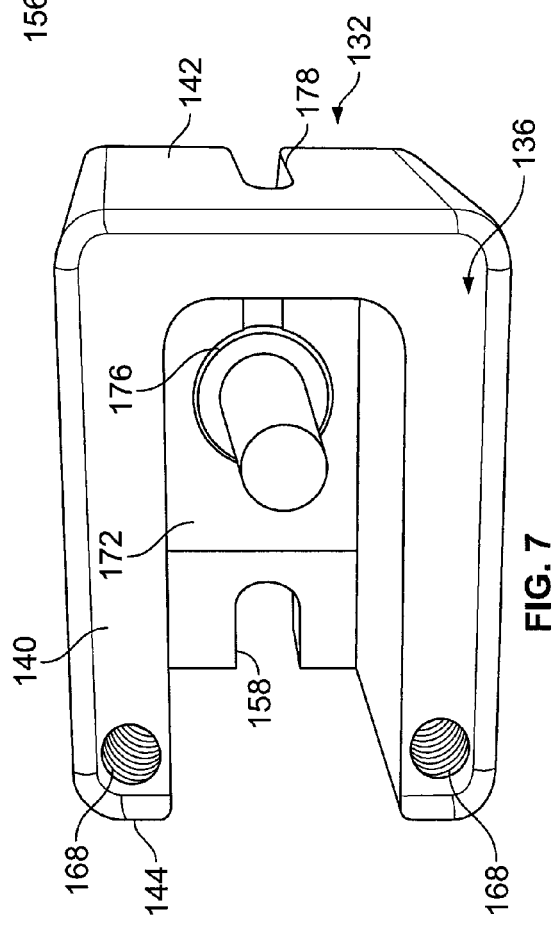
FIG. 8
FIG. 7

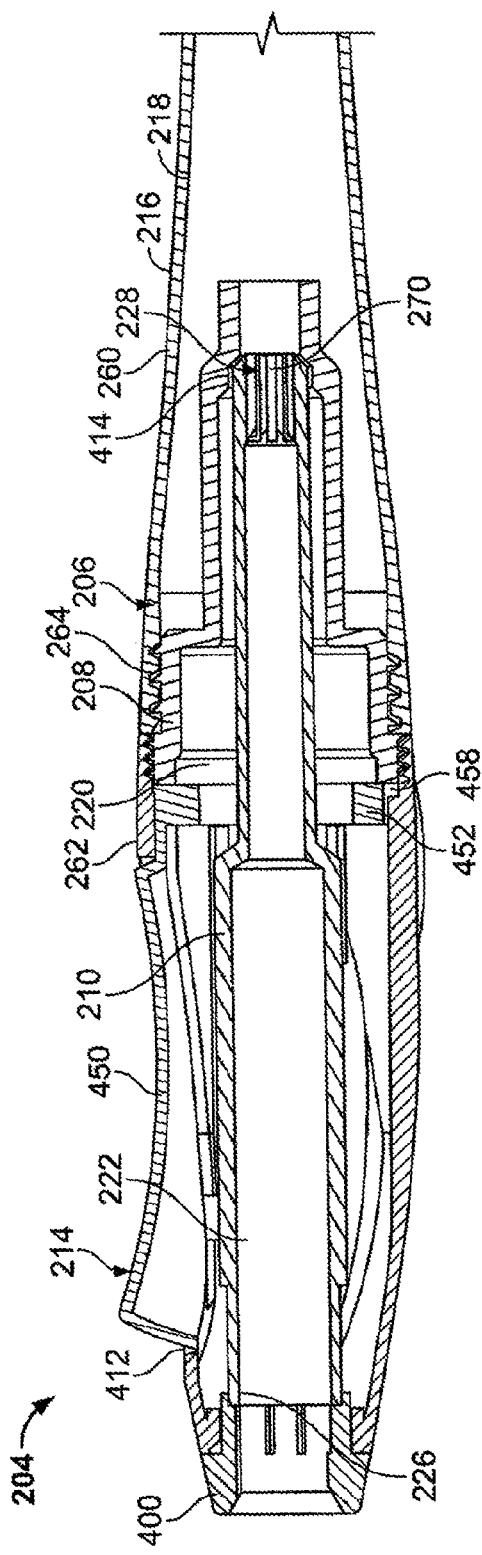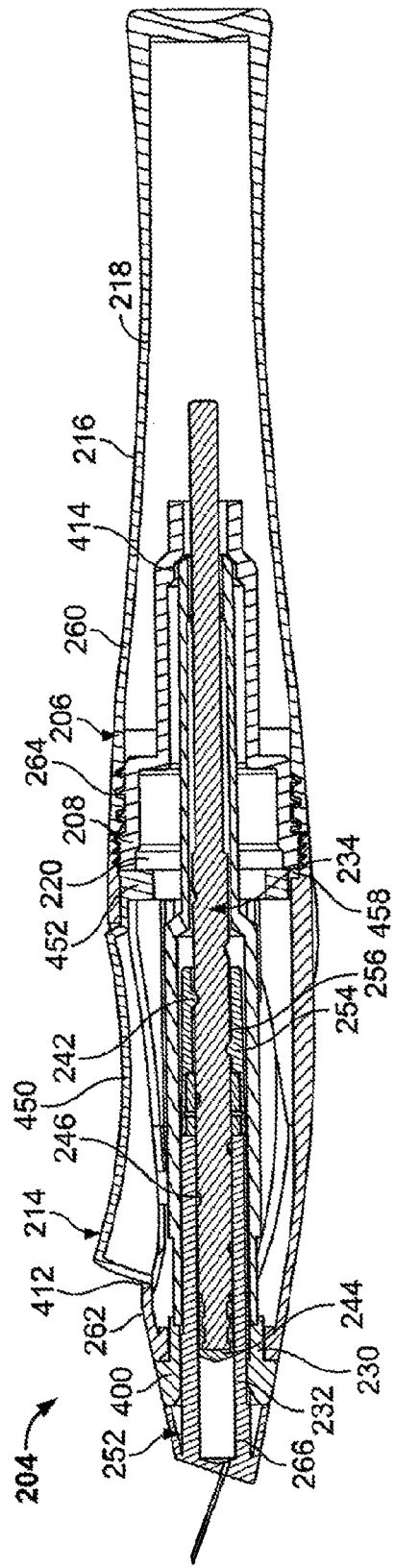

APPARATUS AND METHODS FOR DELIVERING FLUID AND MATERIAL TO A SUBJECT

CROSS-REFERENCE TO RELATED APPLICATIONS

This application claims the benefit of priority of U.S. Provisional Application No. 60/771,915, filed Feb. 9, 2006, U.S. Provisional Application No. 60/791,489, filed Apr. 12, 2006, and U.S. Provisional Patent Application No. 60/803,248 filed May 26, 2006. These applications are incorporated by reference in their entirety.

BACKGROUND OF THE INVENTION

Current methods for injecting small amounts of material are problematic. One solution has been to use micrometer heads along with a syringe to deliver precise small amounts of fluid from a syringe. There are, however, problems with this current technology. Firstly, while commercially available micrometer heads allow for the plunger of a syringe to be depressed, they do not contain a mechanism to "pull back" the plunger in order to aspirate discreet amounts of fluid into a syringe. Secondly, the design of standard micrometer/syringe systems leads to a large arrangement that is unwieldy to operate and often requires two hands to operate, one to hold the syringe steady, the other to operate the micrometer head. The present invention provides a new micrometer assembly that overcomes these problems.

Another problem with injecting small amounts of material such as cells, is the damage that is done to the material when it is injected. When small amounts of cells are injected, the aspiration of cells into a syringe often causes damage to the morphology of the cells, which can impact their viability when injected into a host. Furthermore, when only small amounts of material are injected, the removal of the needle injecting the material can often "pull back" some of the material out of the injection site when removed. The present invention provides new delivery assemblies and methods which overcome these problems.

SUMMARY OF THE INVENTION

The present invention provides fluid and material delivery devices, and methods for delivering fluid and material to a subject.

In one aspect, the present invention provides a method of delivering cellular material into the skin of a subject comprising injecting the cellular material into the skin of a subject such that the injected cells retain their inherent morphologic characteristics upon injection. The method comprises the steps of aspirating the cellular material into a fluid delivery device which incorporates a syringe arrangement. The cellular material is aspirated into the main body of the syringe until the desired amount of a material has filled the syringe body. The needle of the fluid delivery device is then inserted into the skin of a subject at an angle about parallel to the skin until a desired depth has been reached. The cellular material is then injected in the subject until the desired volume of material has been injected. The needle of the device is then rotated approximately 45 to 90 degrees and the needle is removed from the injection site.

In another aspect of the invention, the invention provides delivery devices that can be used to deliver fluid and material using the method of the invention, or other delivery methods.

In one embodiment, the invention comprises a micrometer assisted fluid delivery device comprising a micrometer, a holder portion, and a syringe. The syringe comprises a main body having an interior channel that receives a plunger. The main body of the syringe can optionally have finger tabs. The plunger comprises an elongated shaft, a plunger head and optionally a tabbed end section. The micrometer has a main body, an adjustment thimble and a spindle. The holder portion comprises a main body having a front section and a back section. The main body of the micrometer is attached to the back section of the main body of the holder portion. The main body of the syringe is attached to the front section of the main body of the holder portion and a portion of the plunger is attached to the spindle of the micrometer.

In another embodiment of the micrometer assisted fluid delivery device, the holder portion of the device comprises a main body having a front section, an intermediate section, and a back section. The main body of the holder portion has a top, a bottom and two side walls. The front section of the holder portion has a front face, a back face, side walls that extend from the side walls of the main body, and a syringe body receiving channel. The intermediate section of the holder portion has a front face, a back face, side walls that extend from the side walls of the main body and a syringe plunger receiving channel. The back section of the holder portion has a front face, a back face, side walls that extend from the side walls of the main body and a micrometer receiving aperture that passes from the front face to the back face of the back section. The main body of the micrometer is received by the micrometer receiving aperture of the back section of the holder portion and the main body of the syringe is received by the syringe body receiving channel. The plunger is received by the syringe plunger receiving channel. Finger tabs of the syringe are positioned between the intermediate and the front section of the main body of the holder portion and the spindle of the micrometer is in contact with the tabbed end section of the syringe. The spindle can alternatively be attached to the plunger.

In still another embodiment of the micrometer assisted fluid delivery device, the holder portion of the device comprises a main body having a front face, a back face, a top, a bottom, two side walls, an interior channel, a syringe finger tab channel, a syringe body channel, a syringe plunger channel and a micrometer receiving aperture which passes through the back face of the main body to the interior channel of the main body. The main body of the micrometer is received by the micrometer receiving aperture of the holder portion and the main body of the syringe is received by the syringe body receiving channel of the holder portion. The plunger is received by the syringe plunger channel of the holder portion and the finger tabs of the syringe are received by the syringe finger tab channel. The spindle of the micrometer is in turn in contact with the tabbed end section of the syringe. The spindle can alternatively be attached to the plunger. In one embodiment, the spindle is attached by way of a syringe plunger holder. The syringe plunger holder comprises a main body having a front face, a back face, a side wall, a syringe tabbed end section channel which receives the syringe tabbed end section, a syringe plunger channel which receives the syringe plunger, and a spindle channel which receives the spindle of the micrometer. The main body of the syringe plunger holder can further contain a spindle securing threaded aperture that receives a screw which can be tightened to secure the spindle of the micrometer.

In yet another embodiment of the micrometer assisted fluid delivery device, the device comprises a micrometer and a syringe as described above, and a holder portion and a syringe plunger yoke. The holder portion comprises a main body having a front face, a back face, a top, a bottom, side walls, a syringe body channel, a plunger yoke channel, and a micrometer receiving aperture located on the front face and passing through to the plunger yoke channel. The syringe plunger yoke comprises a main body having a front face, a back face, a top, a bottom and side walls. The main body of the micrometer is received by the micrometer receiving aperture of the holder portion and the main body of the syringe is received by the syringe body channel of the holder portion. Both the plunger and the spindle of the micrometer are attached to the syringe plunger yoke. In one embodiment, the plunger of the syringe is received by a syringe plunger channel located on the bottom of the syringe plunger yoke. When the syringe has a tabbed end section, the tabbed end section can be received by a syringe plunger tabbed end section channel located on the bottom of the syringe plunger yoke. When the syringe has finger tabs, the finger tabs can be received by a syringe tab channel in the main body of the holder portion. In this arrangement, the device can further comprise a syringe holder block which is also received by the syringe tab channel. The syringe block holder has a syringe plunger channel that receives the syringe plunger. The syringe plunger block secures the finger tabs of the syringe to the main body of the holder portion by pressure exerted on the syringe plunger block by a spring located in a spring channel located in the main body of the holder portion. The spring channel extends from the back face of the main body of the holder portion to the syringe tab channel. Another optional feature of this embodiment of the fluid delivery device is that the spindle of the micrometer is attached to the syringe plunger yoke within a spindle receiving aperture, the spindle being friction fit within the spindle receiving aperture.

In another embodiment of the invention, the micrometer assisted fluid delivery devices described above can be used to deliver material into a subject by a method comprising first aspirating a material into the fluid delivery device by turning the micrometer thimble until the desired amount of a material has filled the syringe body of the fluid delivery device. Next, the needle of the fluid delivery device is inserted into the skin of a subject at an injection site at an angle about parallel to the skin of the subject at the injection site until a desired depth has been reached. The material is then injected into the subject by turning the micrometer adjustment thimble, in increments, until the desired volume has been injected. The fluid delivery device, and in turn the needle of the device, is then rotated approximately 45 to 90 degrees and then the needle is removed from the injection site.

In another embodiment of the invention, the invention provides a fluid delivery device comprising a housing body, a pinion housing, a pinion, a detachable syringe cartridge, and a trigger portion on the housing body. The housing body has an exterior and an interior with the pinion housing secured on the interior of the housing body. The pinion housing has an aperture designed to receive the pinion. The pinion is in turn secured to the pinion housing so that it can rotate within the pinion receiving aperture. The pinion itself has a front section having gear ridges, a syringe cartridge receiving aperture and a rear section. The syringe cartridge comprises a head portion, a syringe body, a main portion, a plunger and a needle. The head portion of the syringe cartridge engages with a portion of the housing body to secure the syringe cartridge to the housing body. The head portion is attached to the syringe body which has an interior channel. The syringe body is connected to the main body portion of the cartridge. The main body of the cartridge also has an interior channel which is aligned with the interior channel of the syringe body. The interior channel of the main body has a threaded portion. The plunger of the syringe cartridge is received by the interior channels of the syringe body and the main body. The plunger has a plunger tip, a threaded screw section which engages with the threaded portion of the interior channel of the main body in a screw like fashion, and a tail section. The tail section of the plunger is received by the syringe receiving aperture of the pinion and engages with the rear section of the pinion such that when the pinion is turned the syringe plunger is turned and moves forward in the syringe body. The needle of the syringe cartridge is attached to the head portion and is operatively connected to the interior channel of the syringe body. The trigger portion of the device has a tab section which is adapted to engage with a gear ridge of the pinion when depressed, the trigger portion being attached at one end to the pinion housing.

In another embodiment of the invention, the fluid delivery device described above can be used to deliver material into a subject by a method comprising first loading a syringe cartridge into the housing body of the fluid delivery device, wherein the syringe body is filled with a desired amount of material. The needle of the fluid delivery device is inserted into the skin of a subject at an injection site at an angle about parallel to the skin of the subject at the injection site until a desired depth has been reached. The material is then injected into the subject by depressing the trigger portion of the fluid delivery device. The fluid delivery device, and in turn the needle of the device, is then rotated approximately 45 to 90 degrees and then the needle is removed from the injection site.

In another embodiment of the invention, the invention comprises a cellular material delivery device. The cellular material delivery device comprises an elongated shaft having a diameter, a latitudinal axis, a circumference and proximal, medial and distal portions. The distal portion of the device has a sharpened point and the medial portion of the device has a series of annular grooves that run around the circumference of the shaft. These grooves can be helically orientated in one embodiment. Optionally, the elongated shaft can further have an axial channel that runs along a portion of the shaft and onto the sharpened point.

The cellular material delivery device can be used, in one embodiment, to deposit cellular material under the surface of the skin of a subject. The method comprises depositing the cellular material on the surface of the skin of a subject at an injection site. The skin of the subject is then pierced at the injection cite using the sharpened point of the cellular delivery device. The cellular delivery device is inserted so that the annular grooves of the device pick up the material from the surface and convey this material beneath the surface of the skin. The cellular delivery device is then withdrawn from the subject having deposited the material below the surface of the skin.

BRIEF DESCRIPTION OF THE DRAWINGS

FIG. 7 is a rear view of one embodiment of the holder portion connected to the micrometer.

FIG. 8 is a side view of one embodiment of the holder portion connected to the micrometer.

FIG. 10 is a side cutaway view of one embodiment of the fluid delivery device absent the syringe arrangement.

FIG. 11 is a side cutaway view of one embodiment of the fluid delivery device with the syringe arrangement.

DETAILED DESCRIPTION OF THE INVENTION

Figure 1:
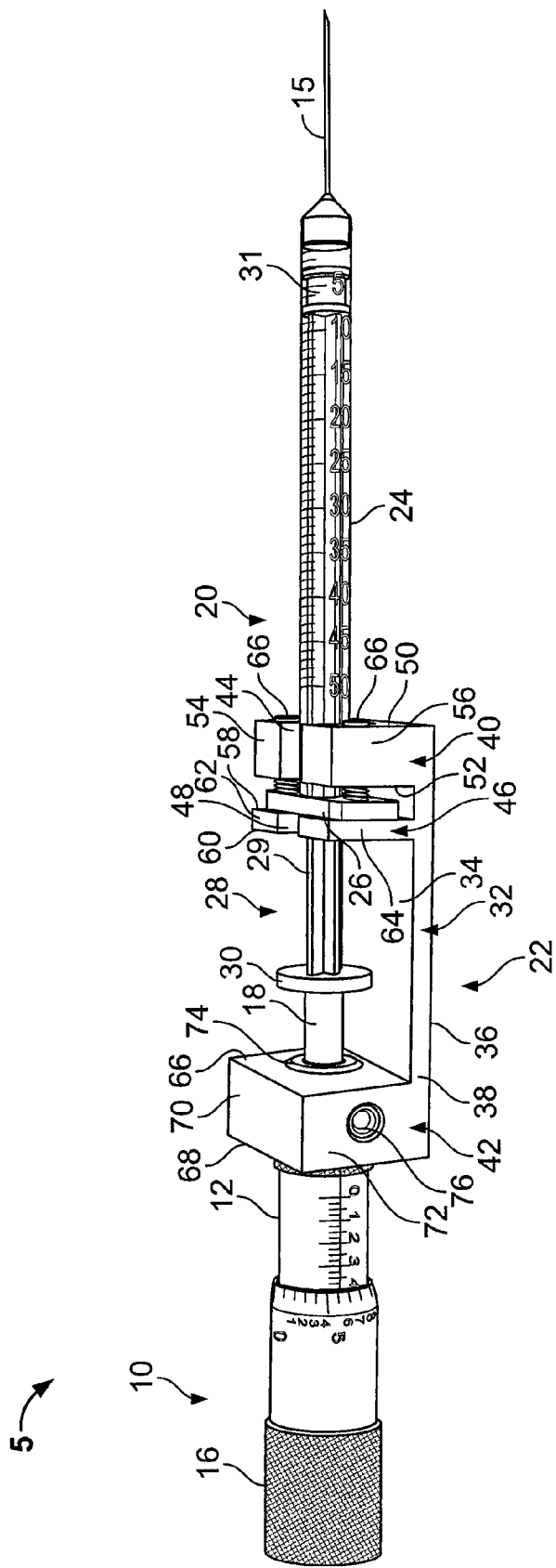
FIG. 1 is a side view of one arrangement of a micrometer assisted fluid delivery device.

Before the embodiments of the invention are explained in detail, it is to be understood that the invention is not limited in its application to the details of construction and the arrangements of the components set forth in the following description or illustrated in the drawings. The invention is capable of other embodiments and of being practiced or being carried out in various ways. Also, it is understood that the phraseology and terminology used herein are for the purpose of description and should not be regarded as limiting. The use of "including", "having", "has" and "comprising" and variations thereof herein is meant to encompass the items listed thereafter and equivalents thereof as well as additional items and equivalents thereof. The use of the term "attached" is meant that the elements listed as attached to each other are either secured to each other, affixed to each other, attached to each other, or integral to each other (i.e., present in the same piece).

The present invention is directed towards fluid and material delivery devices, and methods for delivering fluid and material to a subject. Suitable subjects include mammals, and more suitably include human beings. Suitably, the methods and devices of the present invention are used in hair replacement therapy for the injection and delivery of hair follicle cells under the skin of a subject.

In one aspect, the present invention provides a method of delivering material into a subject in an effective amount to treat a disease or a physical condition which afflicts the subject. Such diseases and physical conditions that can be treated by the method can include hair loss, psoriasis, diabetes, rhytids, skin atrophy, tooth loss, skin ulcers, bed sores, diabetic foot ulcers, burn wounds, microbial infections, surgical scars, acne, and chicken pox.

Material that can be delivered by the method can suitably be fluid compositions or cellular material. Examples of fluid compositions that can be delivered by the method include, but are not limited to, botox, collagen, hyaluronic acid, antibiotics, anti-inflammatory drugs, steroids and combinations thereof. Examples of cellular material that can be delivered by the method include, but are not limited to, dermal cells, epidermal cells, epidermal stem cells, basal cells, keratinocytes, melanocytes, trichogenic dermal cells, fibroblasts, follicular progenitor cells, autologous follicular progenitor cells, pancreatic islet cells, adipose cells, dental epithelial cells, dental dermal cells or any combinations of the cells. Suitably the cells can be in a suspension media. The cells delivered by the method retain their inherent morphologic characteristics upon injection. Such methods allow for the cells to maintain their normal viability and function after delivery. When hair follicle cells are delivered to treat hair loss, the cells are delivered to the skin of a subject, suitably to the skin's sub-epidermal layer, papillary dermal layer or upper reticular dermal layer.

The method comprises the steps of aspirating the material into a delivery device which incorporates syringe arrangement. The material is aspirated into the main body of the syringe until the desired amount of the material has filled the syringe body. The needle of the delivery device is then inserted into the skin of a subject at an angle about parallel to the skin until a desired depth has been reached. The material is then injected in the subject until the desired volume of material has been injected. The needle of the device is then rotated approximately 45 to 90 degrees and the needle is removed from the injection site. By twisting the needle before removal of the needle, any surface tension between the material delivered and the needle is broken or disrupted. This helps prevent the material from flowing back out of the injection site when the needle is removed.

In another aspect, the invention provides delivery devices that can be used to deliver fluid and material using the method of the present invention, or other delivery methods.

One embodiment of the invention provides a micrometer assisted delivery device 5. The micrometer assisted delivery device is designed to control the precise amount of that solution that can be aspirated and delivered by a syringe into tissue. The micrometer assisted delivery device also allows a user to better control the rate of aspiration and dispensement. This fine control of rate and volume allows the user to minimize air within the syringe.

Various embodiments of the micrometer assisted fluid delivery device are depicted in FIGS. 1-8. The micrometer assisted fluid device 5 comprises a micrometer 10, a holder portion 22, 78, 132 and a syringe 20.

The syringe 20 comprises a main body 24 having an interior channel 25 that receives a plunger 28. The main body 24 of the syringe 20 can optionally have finger tabs 26. The plunger 28 comprises an elongated shaft 29, a plunger head 31 and optionally a tabbed end section 30. A needle 15 is operatively connected to the interior channel 35. Different standard syringes can be selected depending on the desired material to be delivered and the therapeutic use and dose desired to be delivered.

The micrometer 10 has a main body 12, an adjustment thimble 16 and a spindle 18. Optionally the micrometer can have a locking collar 14 that can be turned to lock the thimble 16 of the micrometer 10 in place. Any standard, commercially available micrometer can be used. One example is a Micrometer Head available from the L.S. Starrett Company. When the adjustment thimble 16 is rotated, the spindle 18 moves forward or back from the body 12 of the micrometer 10, depending on the direction of the rotation of the adjustment thimble 16. The adjustment thimble 16 can optionally contain markings which indicate the amount the spindle 18 is moving based on the amount the thimble 16 is rotated. Suitably, the present invention utilizes a micrometer 10 that contains a non-rotating spindle.

The present invention provides many different embodiments of the micrometer assisted delivery device 5. The various embodiments have different arrangements of the holder portion with respect to the syringe 20 arrangement and the micrometer 10.

One embodiment of the micrometer assisted delivery system 5 is shown in FIG. 1. In this embodiment the holder portion 22 comprises a main body 32 having a top 34, a bottom 36 and two side walls 38 extending from the bottom 36 to the top 34. The main body 32 is suitably made from a material such as plastic, metal or a ceramic or other composite.

The main body 32 has a front section 40 and a back section 42. The front section 40 of the main body 32 has a front face 50, a back face 52, a top 54, side walls 56 that extend upward to the top 54 from the side walls 38 of the body 32, and a syringe body channel 44 dimensioned to receive the main body 24 of a syringe 20. Alternatively the front section 40 of the main body 32 can have a syringe body receiving aperture that can receive the main body 24 of the syringe 20. The main body 24 of the syringe 20 is attached to the front section 40 of the main body 32. In one embodiment the main body 24 of the syringe 20 is attached to the front section 40 of the main body 32 by a friction fit between the main body 24 of the syringe 20 and the walls of the syringe body channel 44 or a syringe body receiving aperture in the front section 40.

The main body 32 can also alternatively further comprise an intermediate section 46 that has a front face 58, a back face 60, a top 62 and side walls 64 that extend upward to the top 62 from the side walls 38 of the main body 32. The intermediate section also has a syringe plunger channel 48 dimensioned to receive the plunger 28 of a syringe 20. The finger tabs 26 of the syringe body 24 are placed between the intermediate section 46 and the front section 40. The front face 50 of the front section 40 has two threaded channels 66 that allow for a screw to pass through each of them respectively, the screws coming into contact with the finger tabs 26 of the syringe body 24, securing the tabs 26 against the front face 58 of the intermediate section 46.

The back section 42 of the main body 32 has a front face 66, a back face 68, a top 70, and two side walls 72 that extend upward to the top 70 from the side walls 38 of the body 32. The back section 42 also has a micrometer receiving aperture 74 that passes from the back face 68 of the back section 42 to the front face 66 of the back section 42. The micrometer receiving aperture 74 is dimensioned to allow the spindle 18 of the micrometer 10 to pass through the aperture 74, and to receive at least a portion of the micrometer 10. The main body 12 of the micrometer 10 can be attached to the back section 42 of the main body 32. In one embodiment the main body 12 of the micrometer 10 is attached to the back section 42 of the main body 32 by a friction fit between the main body 12 of the micrometer 10 and micrometer receiving aperture 74. In another embodiment, the back section 42 of the holder 22 can have a micrometer securing threaded aperture 76 in the side wall 72 of the section 42 that exits in the interior of the micrometer channel 74. When the micrometer head 10 is received by the micrometer channel 74, a screw can be received by the micrometer securing threaded aperture 76, and the screw can be tightened against the micrometer head 10, until the micrometer head 10 is secured against the holder 22.

The micrometer adjustment thimble 16 can then be turned until the spindle 18 makes contact with the plunger 28, or optionally the tabbed end section 30 of the plunger 28. The spindle 18 of the micrometer 10 can be attached to either the plunger 28 or the tabbed end section 30 of the plunger 28.

Figure 2:
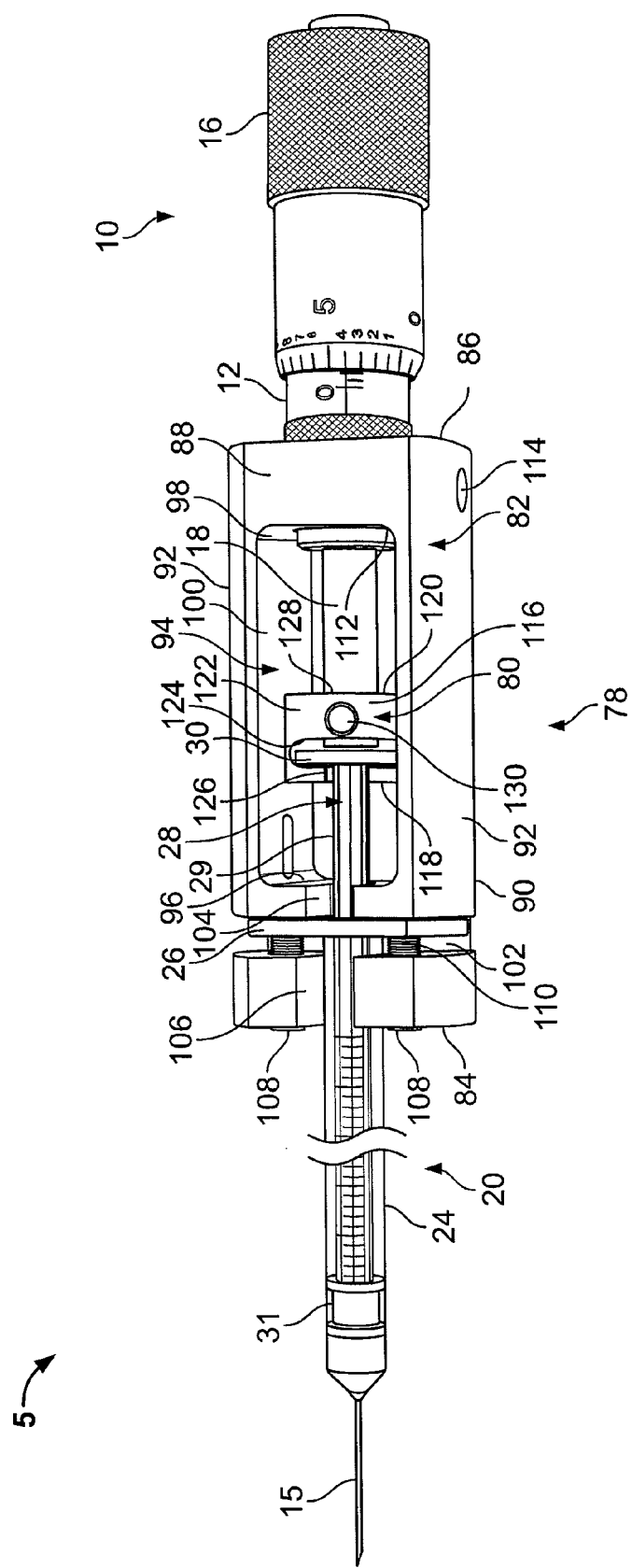
FIG. 2 is a side view of another arrangement of a micrometer assisted fluid delivery device.
Figure 3:
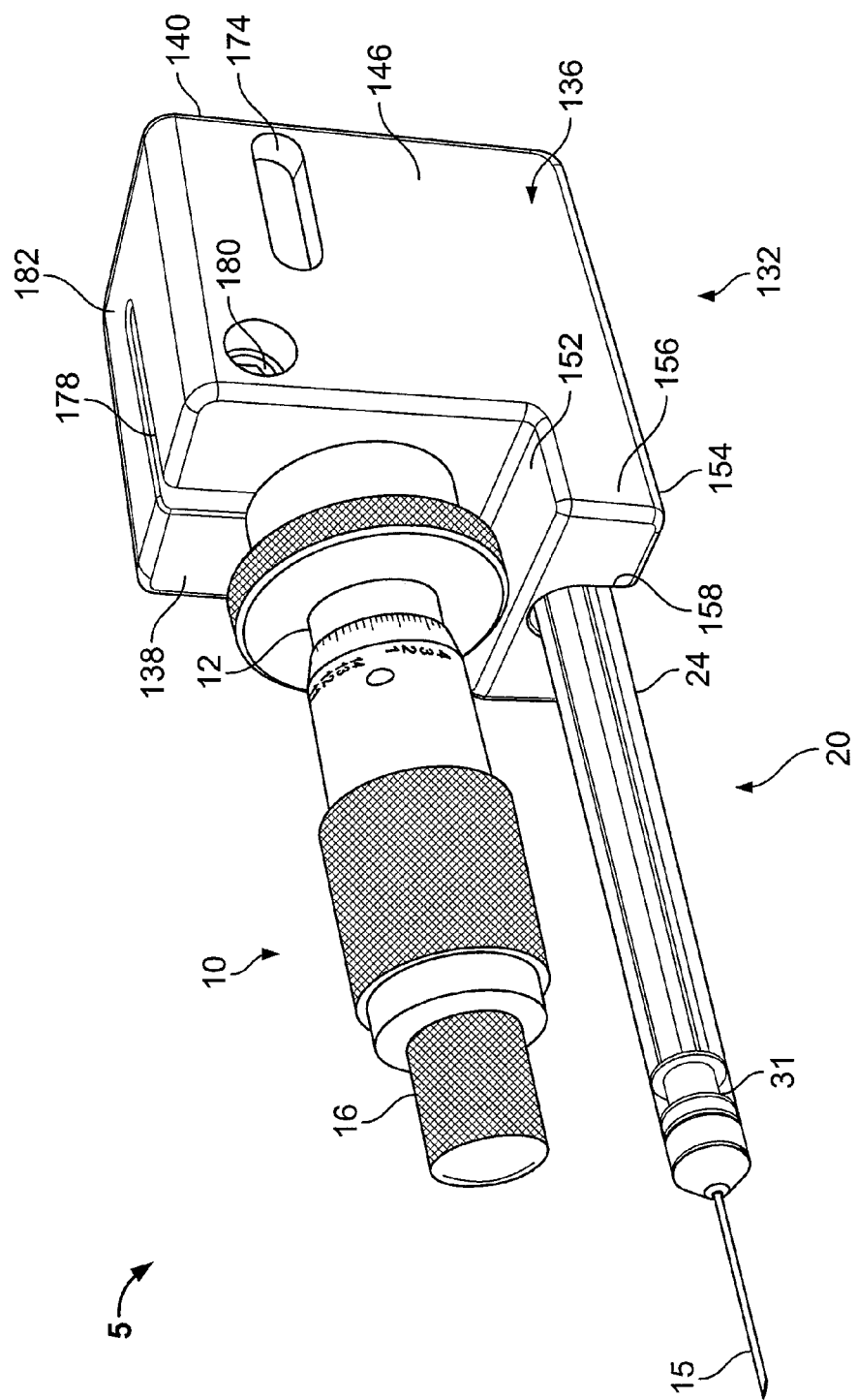
FIG. 3 is a side perspective view of another arrangement of a micrometer assisted fluid delivery device showing the holder portion connected to the micrometer head and syringe.
Figure 4:
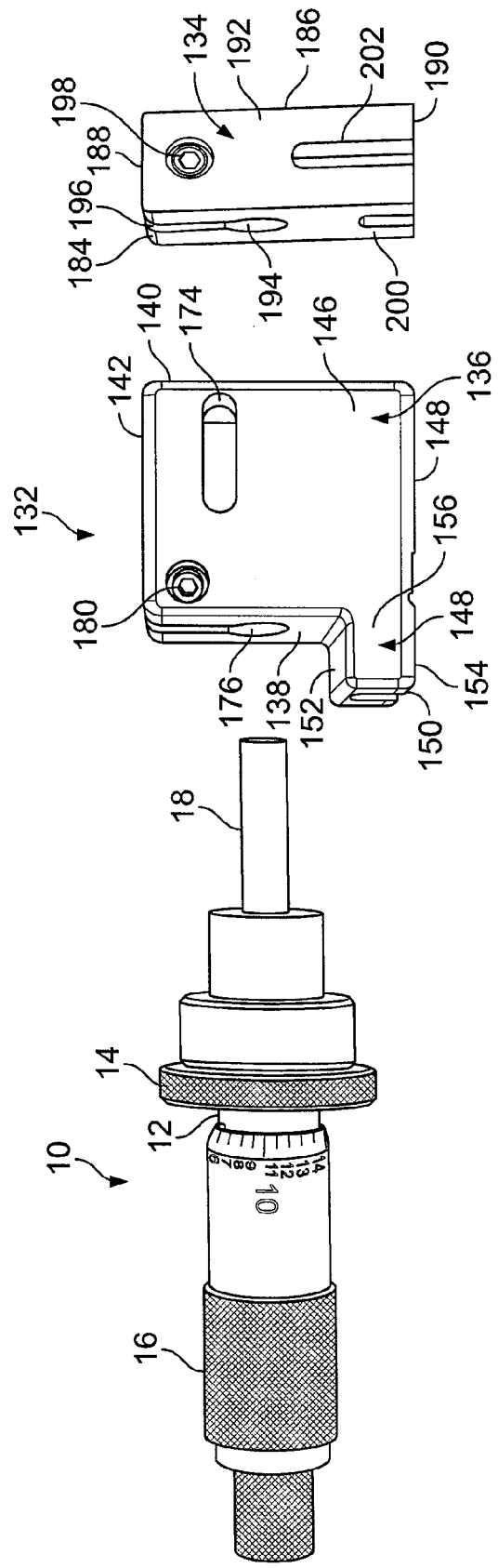
FIG. 4 is a side exploded view of a holder portion and syringe plunger yoke of one embodiment of the micrometer.
Figure 5:
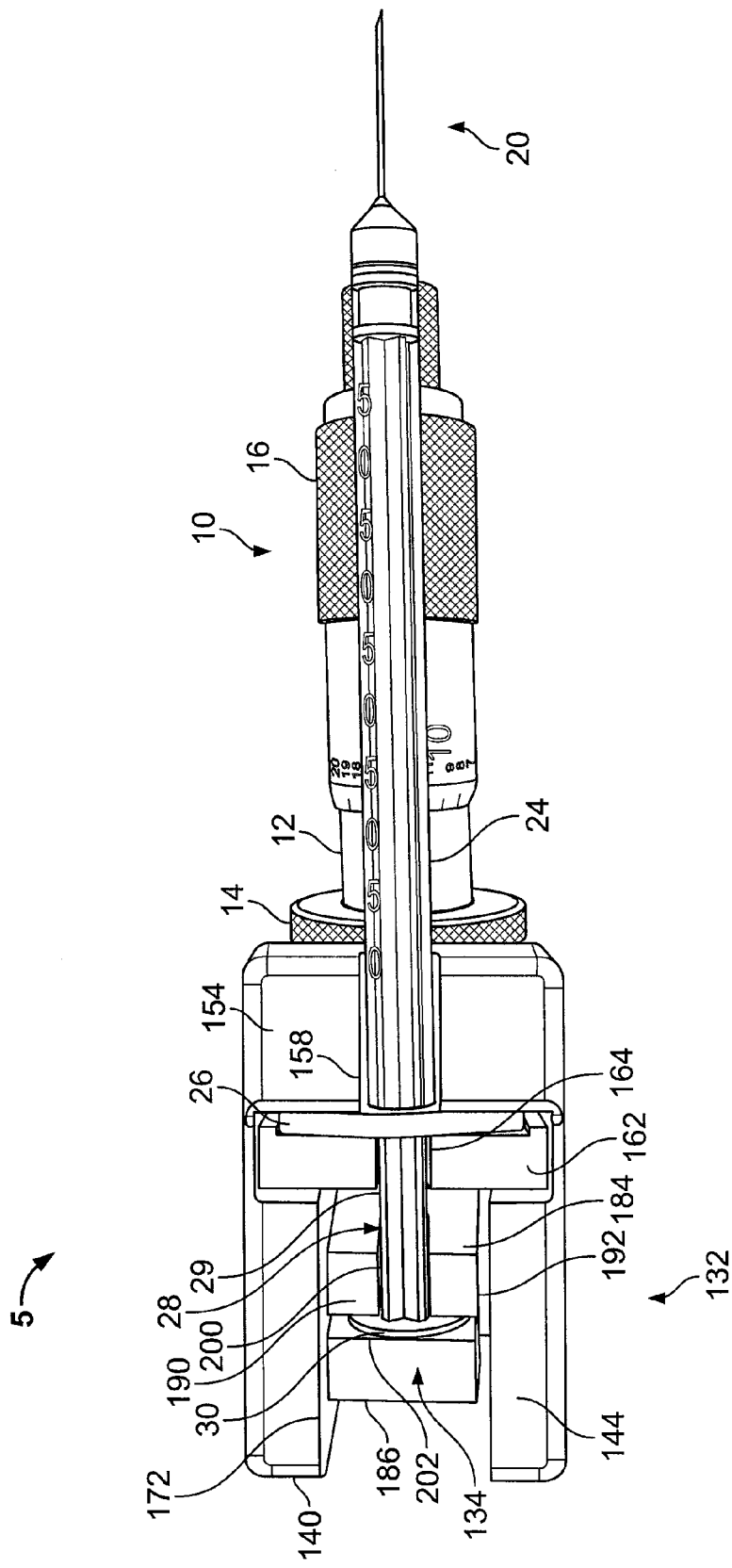
FIG. 5 is a bottom view of one arrangement of a micrometer assisted fluid delivery device showing the holder portion with a syringe secured in the holder portion by the syringe holder block.
Figure 6:
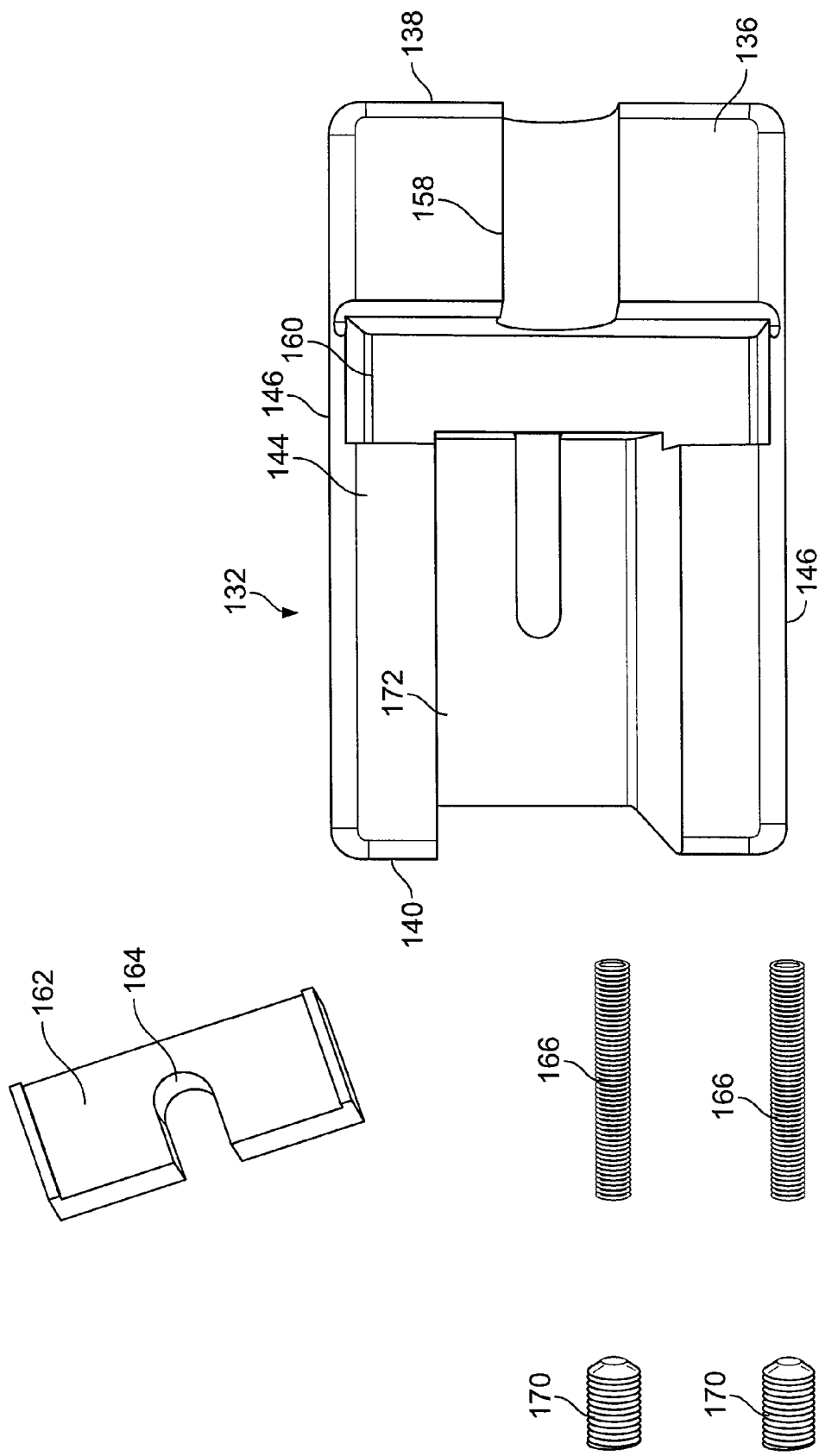
FIG. 6 is a bottom view of one embodiment of the holder portion, the syringe holder block, springs and screws.
Figure 9:
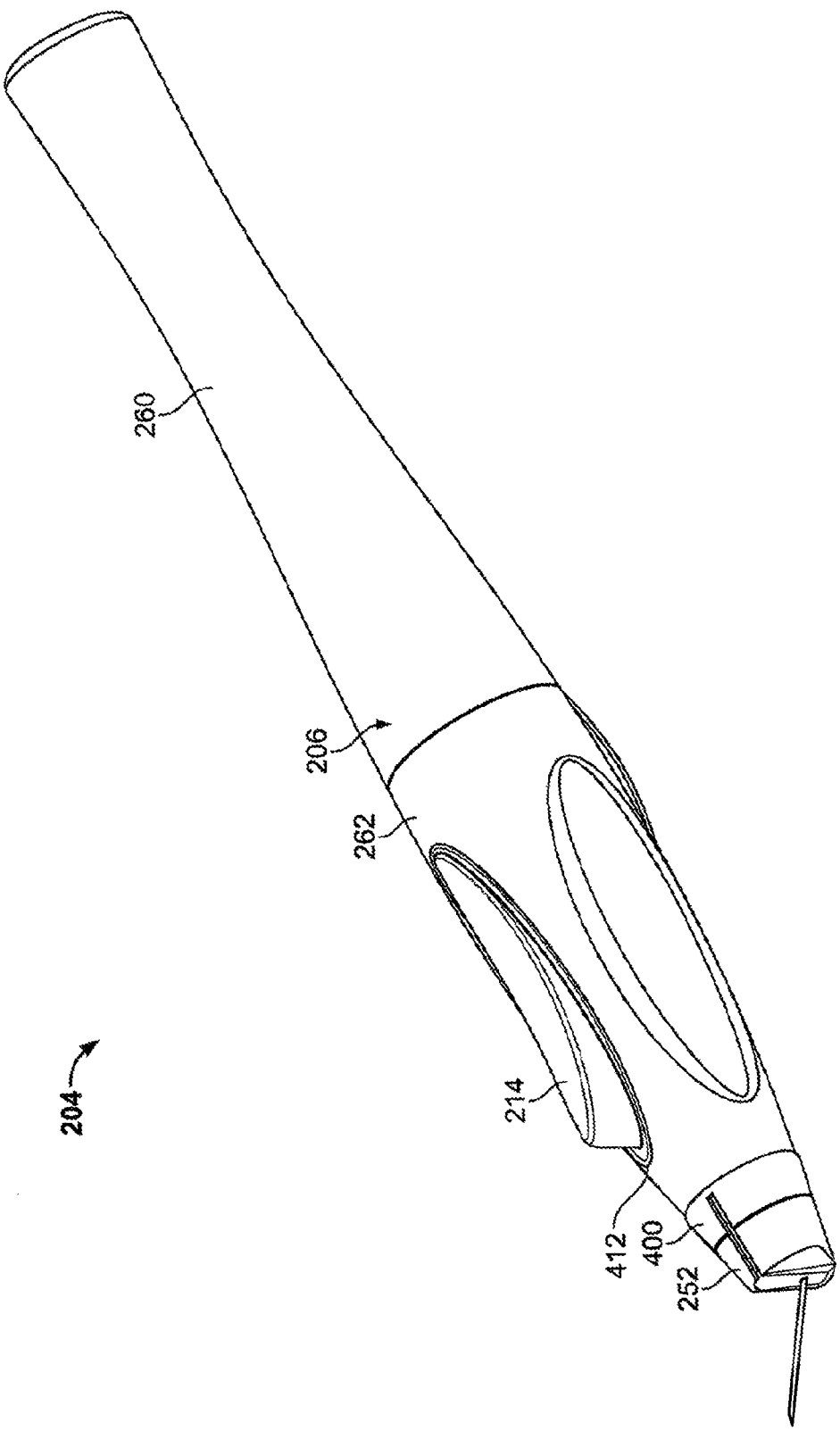
FIG. 9 is a side perspective view of one embodiment of the fluid delivery device.
Figure 12:
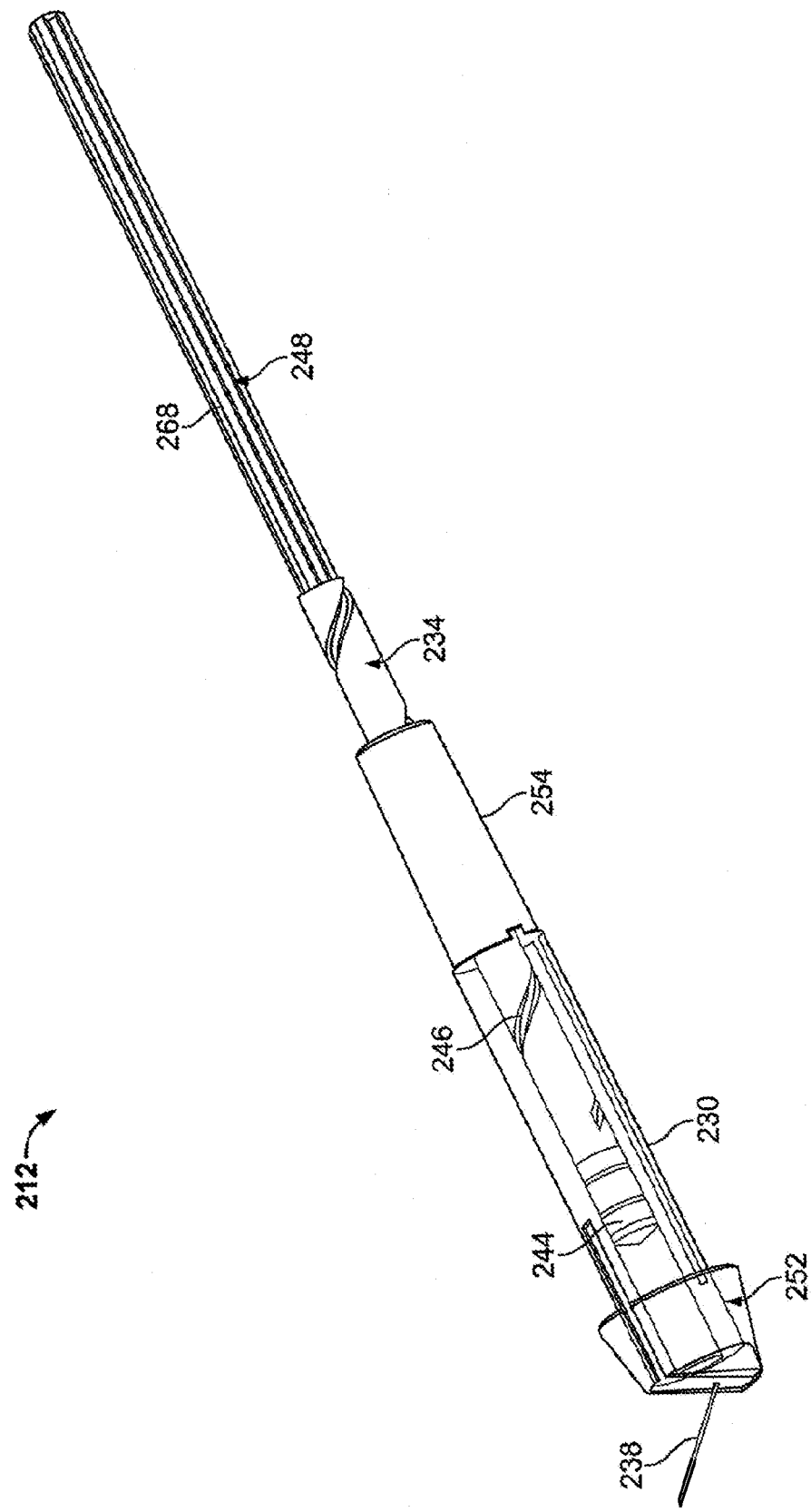
FIG. 12 is a side view showing an embodiment of a detachable syringe cartridge.
Figure 13:
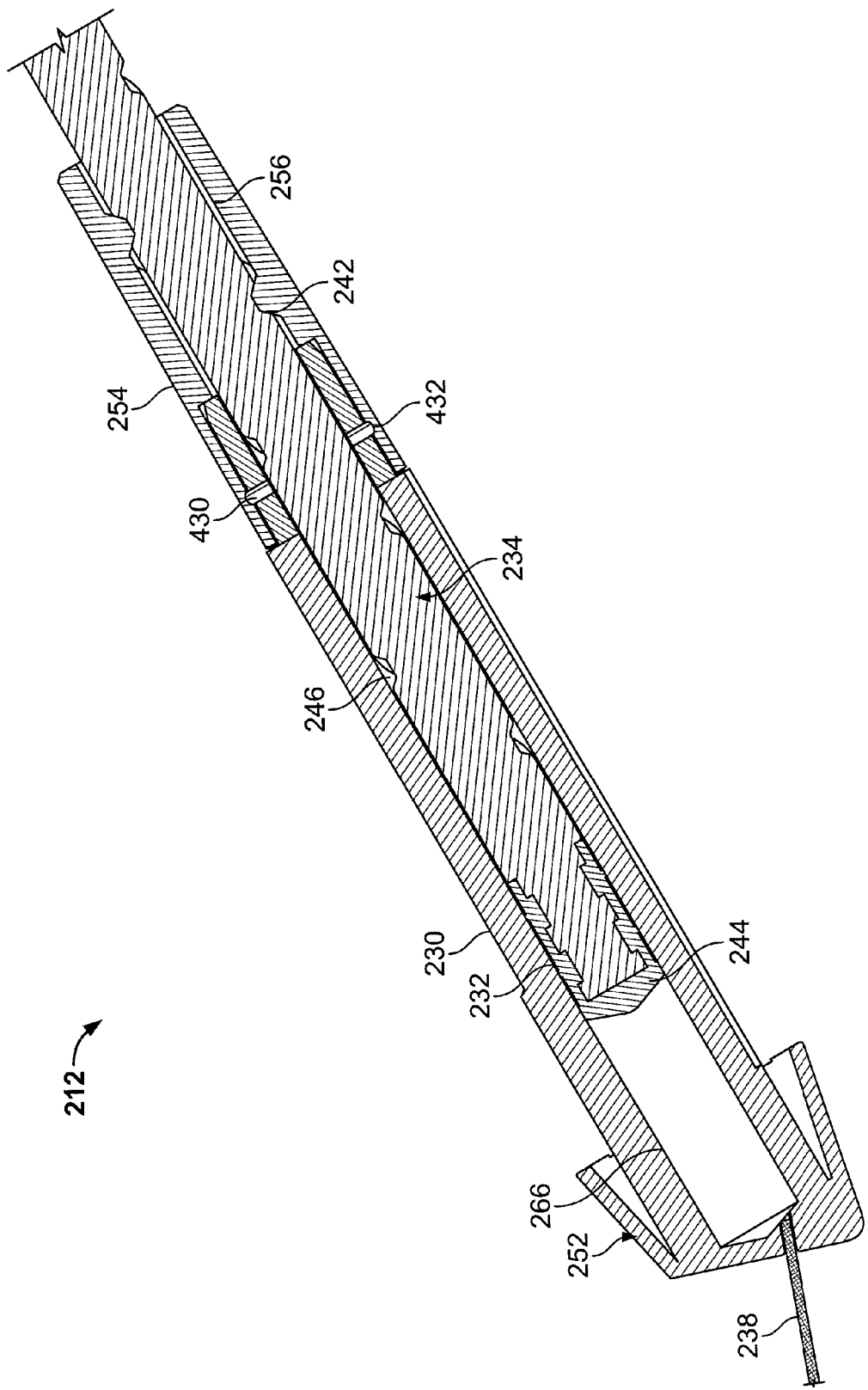
FIG. 13 is a cutaway side view of the detachable syringe cartridge.
Figure 14:
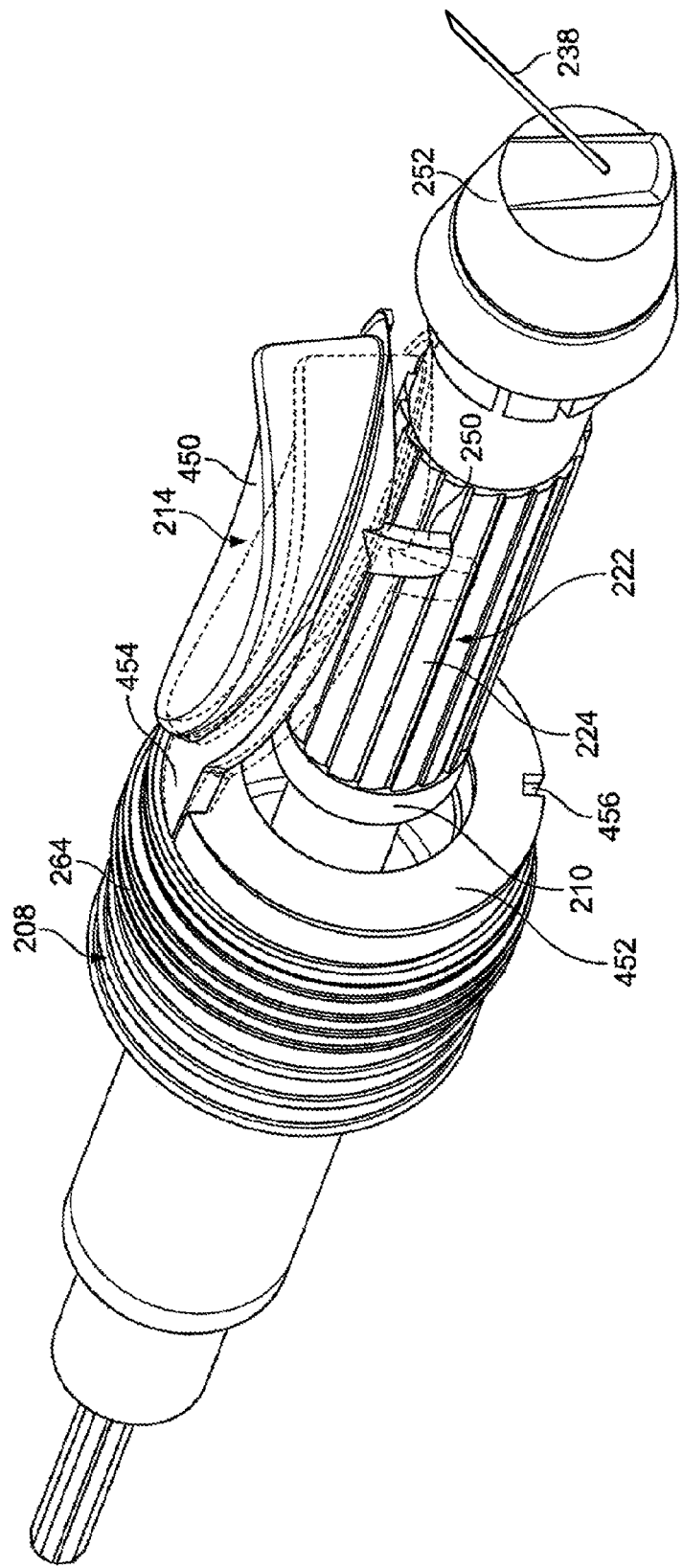
FIG. 14 is a side perspective view of the pinion holder, pinion, syringe arrangement and the trigger portion of the fluid delivery device.
Figure 15:
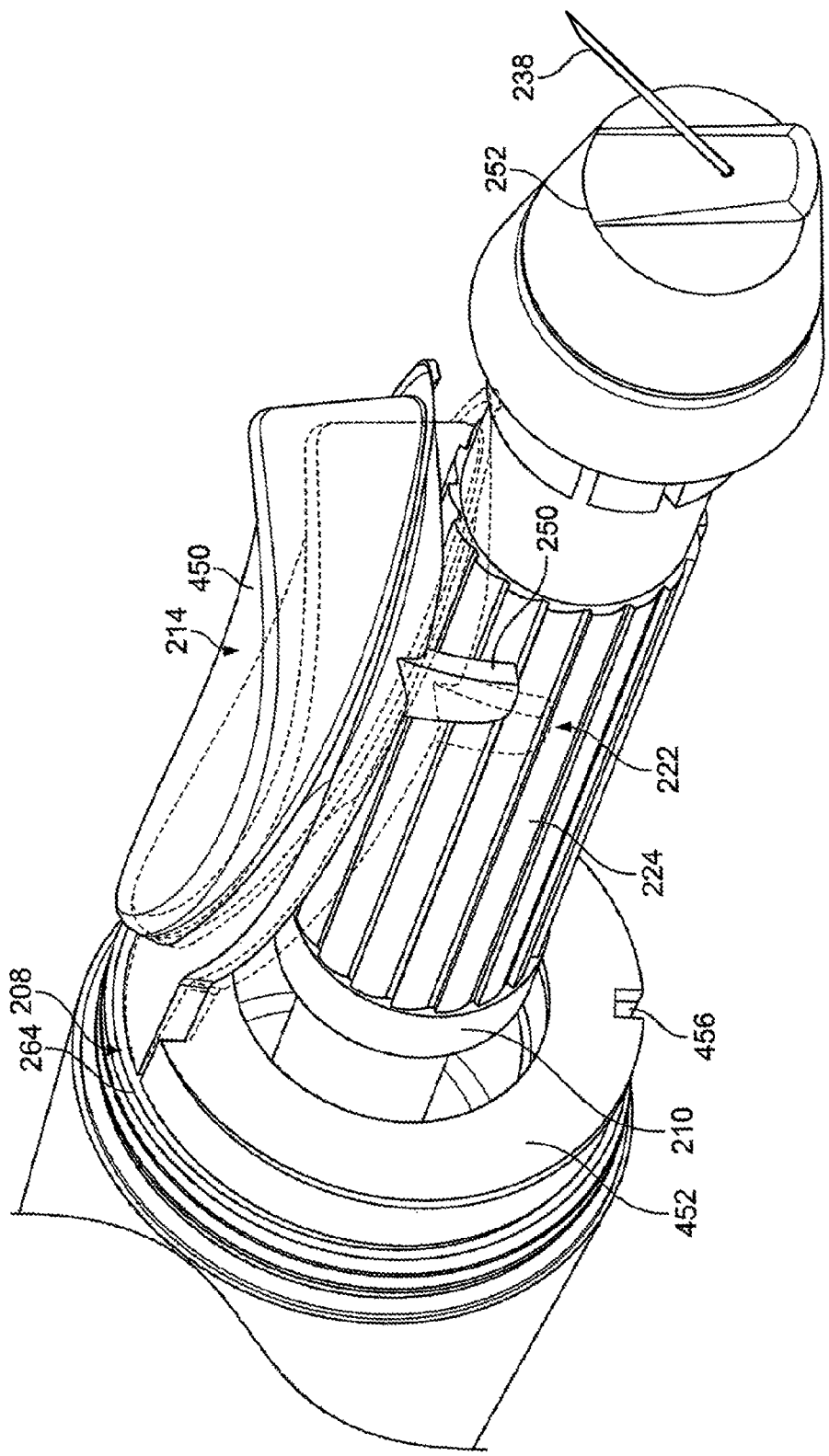
FIG. 15 is a side perspective view of the pinion holder, pinion, syringe arrangement and the trigger portion of the fluid delivery device.
Figure 16:
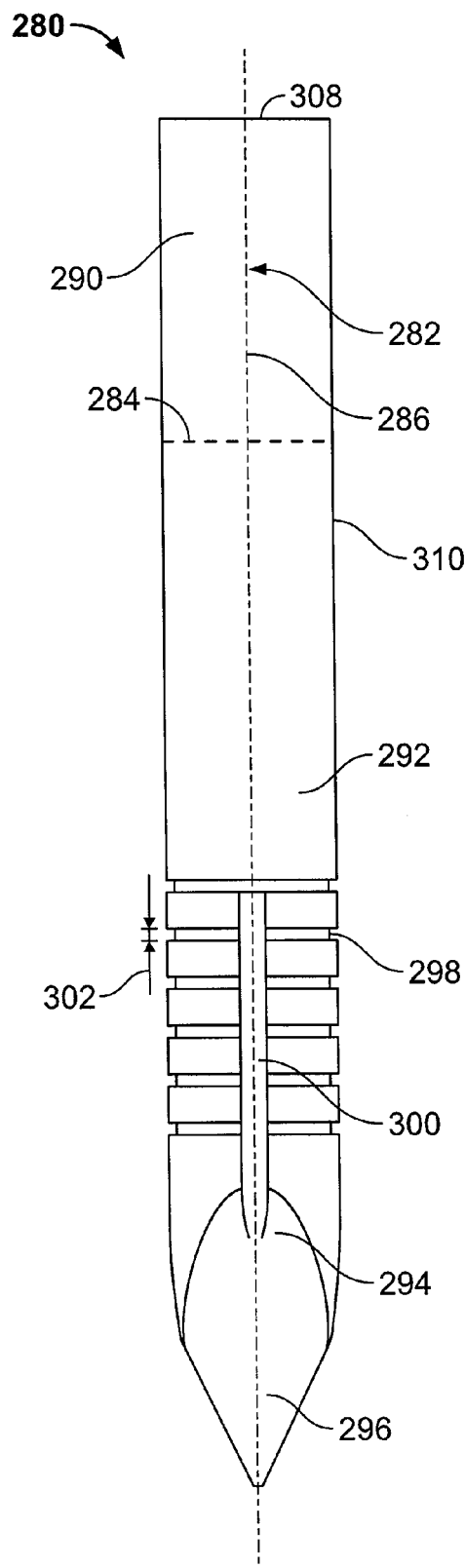
FIG. 16 is a frontal perspective view of one embodiment of the cellular material delivery device.
Figure 17:
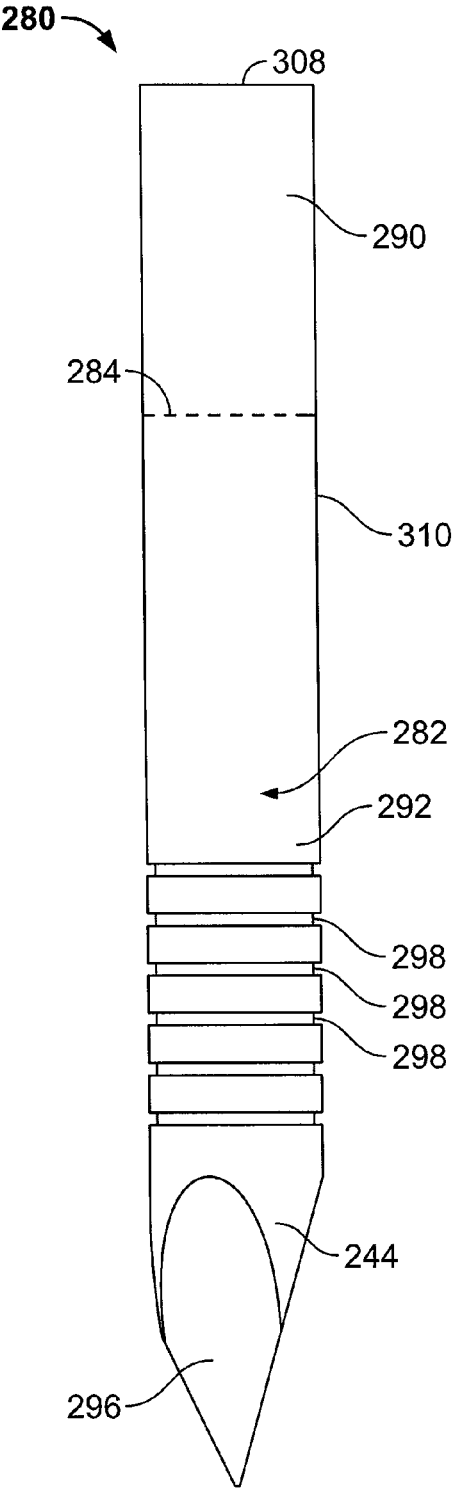
FIG. 17 is a perspective view of the embodiment of the cellular material delivery device shown in FIG. 16 in which the apparatus has been rotated 90° from that shown in FIG. 16.
Figure 18:
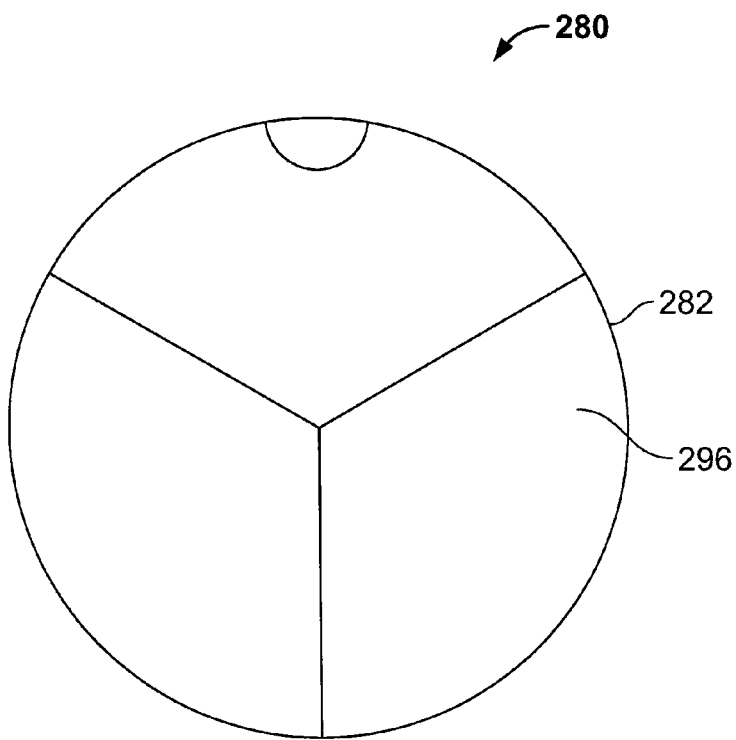
FIG. 18 is a depiction of the cellular material delivery device from the skin-piercing end of the embodiment shown in FIG. 16.
Figure 19:
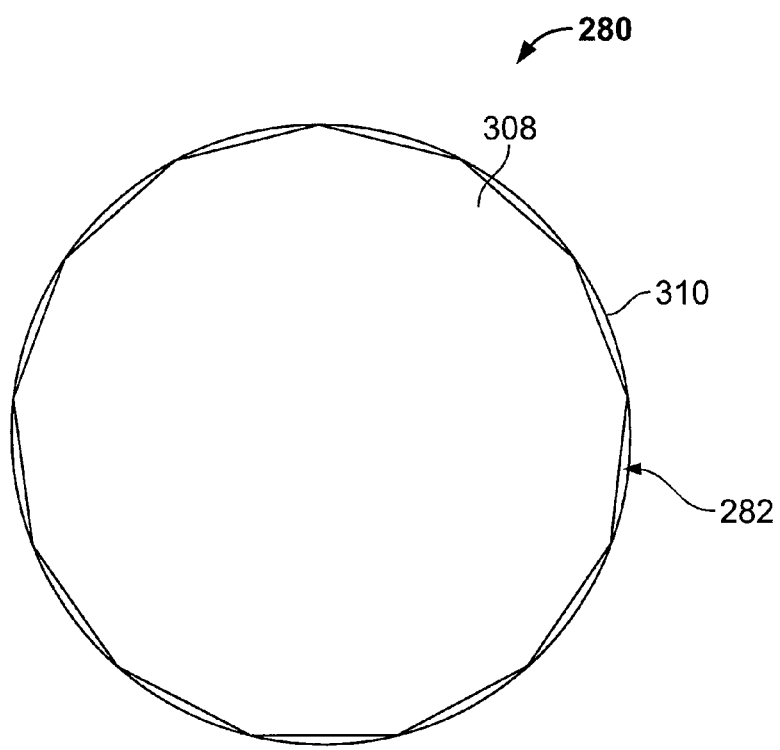
FIG. 19 is an embodiment of the cellular material delivery device shown in FIG. 16 taken from the top of FIG. 16.
Figure 20:
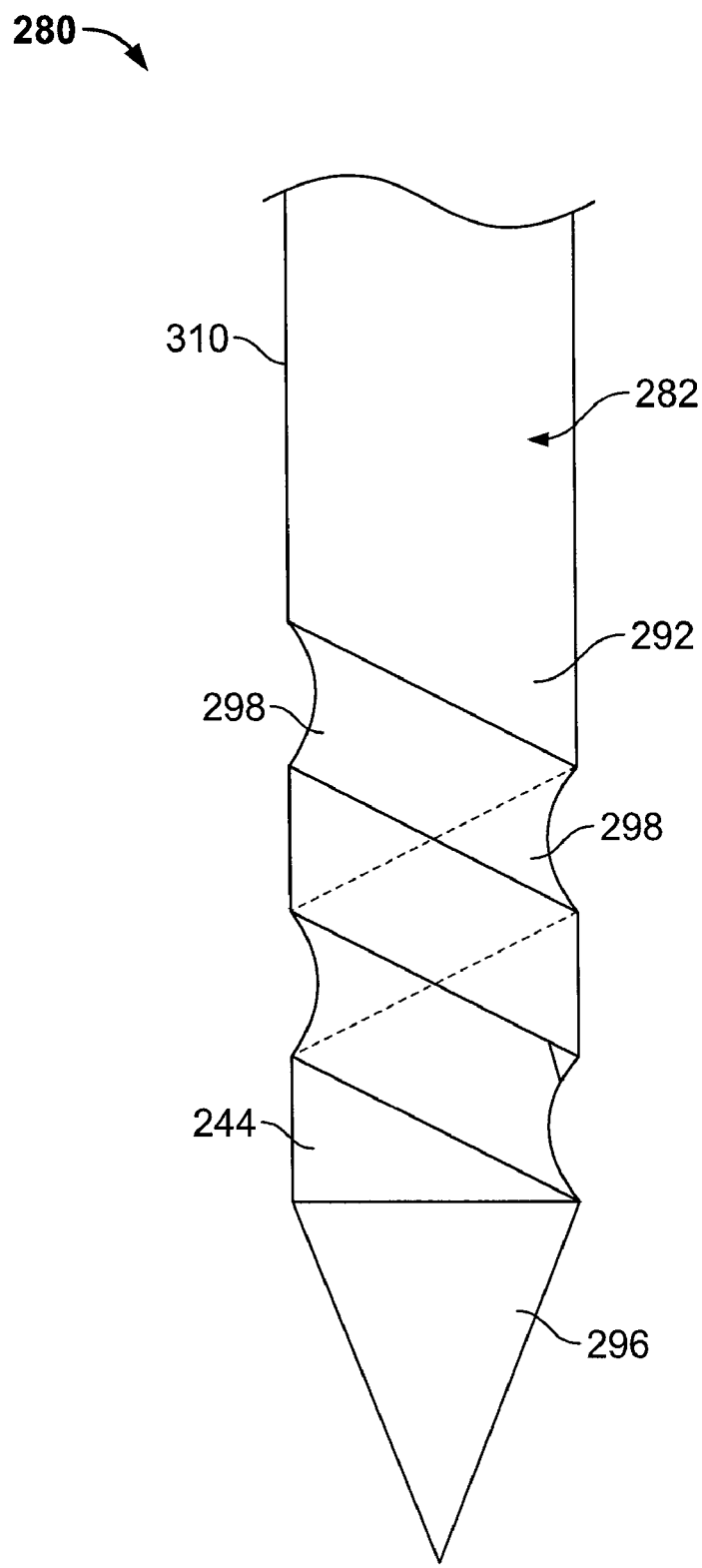
FIG. 20 is a perspective view of another embodiment of the cellular material delivery device.
Figure 21:
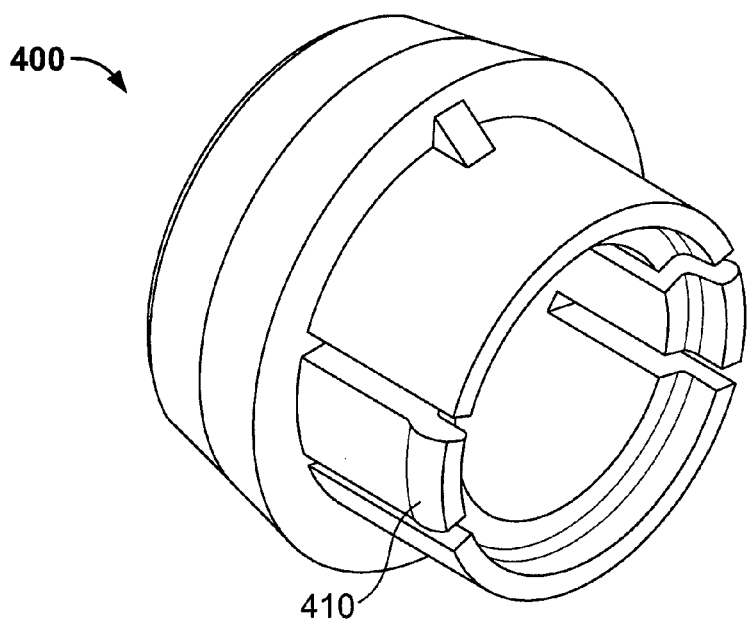
FIG. 21 is a perspective side view of the ring head portion of the fluid delivery device.
Figure 22:
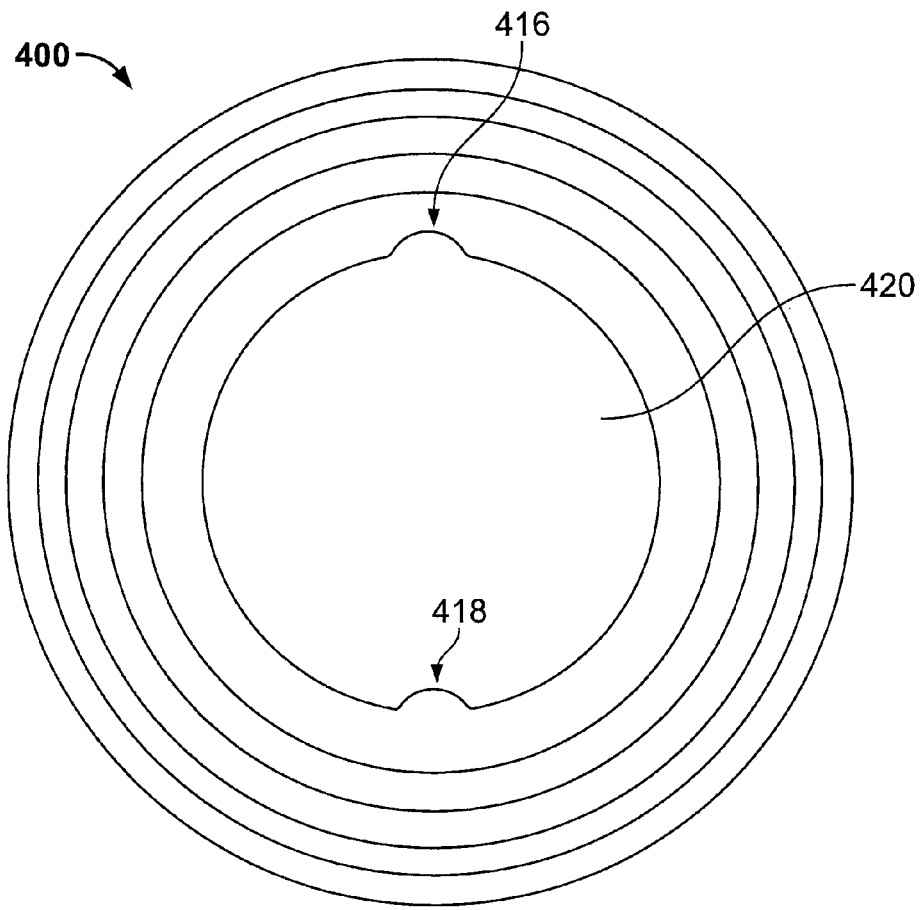
FIG. 22 is an end view of the ring head portion of the fluid delivery device.
Figure 23:
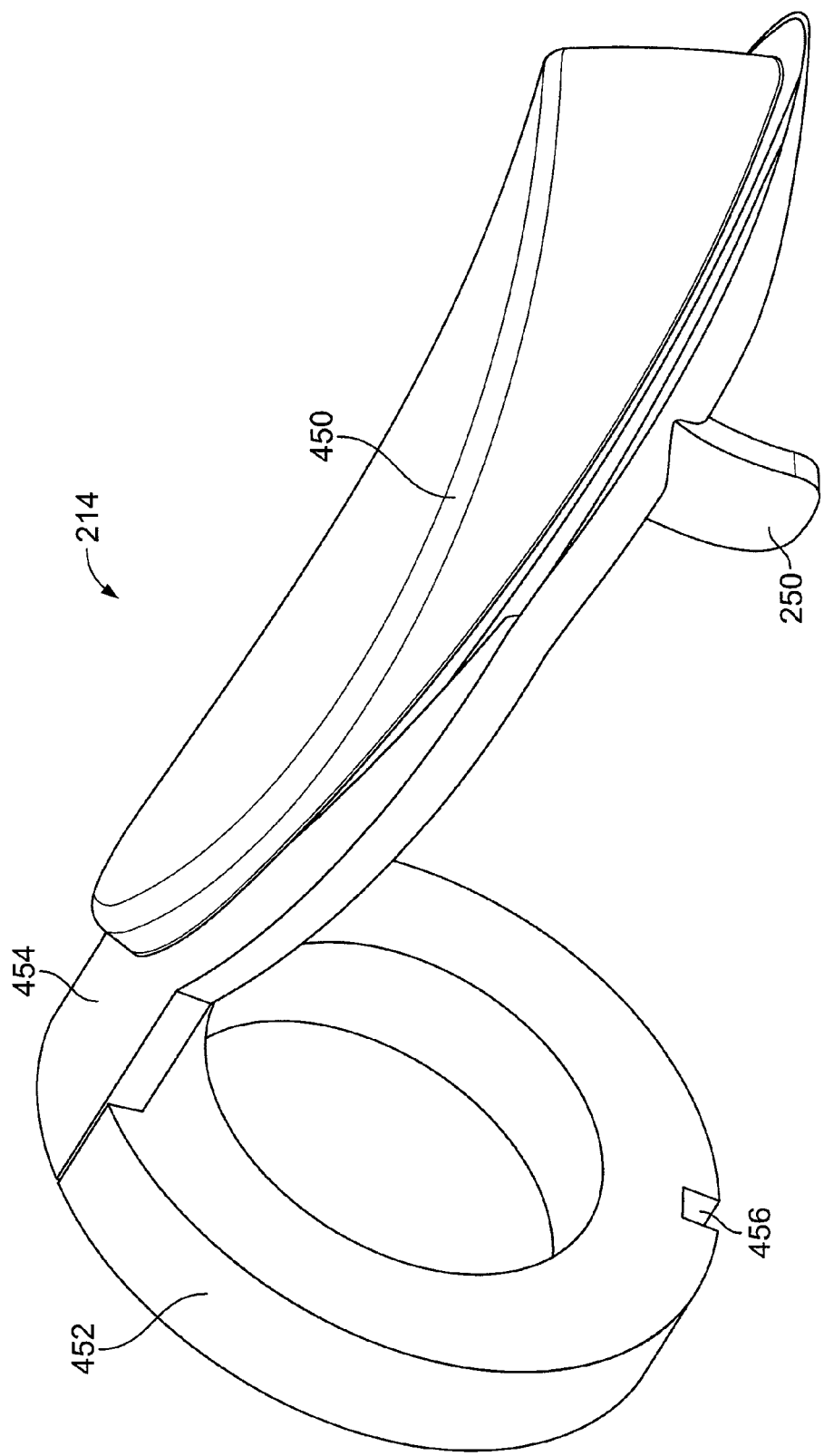
FIG. 23 is perspective view of the trigger portion of the fluid delivery device.

Another embodiment of the micrometer assisted delivery system 5 is shown in FIG. 2. The holder portion 78 comprises a main body 82 having a front face 84, a back face 86, a top 88, a bottom 90 and two side walls 92 extending from the bottom 90 to the top 88. The main body 82 can be made from any suitable material, including metal, plastic, ceramics or other composites. The main body 82 further has an interior channel 94 having a front interior end wall 96, a back interior end wall 98 and interior side walls 100. The interior channel 94 passes through the top 88 and bottom 90 of the body 82. The main body 82 further can comprise a syringe finger tab channel 102 which is dimensioned to receive finger tabs 26 of a syringe body 24. The main body 82 can further comprise a syringe plunger channel 104 which is dimensioned to receive a plunger 28 of a syringe 20, and a syringe body channel 106 dimensioned to receive the body 24 of a syringe 20. The main body 24 of the syringe 20 can be attached to the main body 82. In one embodiment the main body 24 of the syringe 20 is attached to the main body 82 by a friction fit between the main body 24 of the syringe 20 and the walls of the syringe body channel 106. Also, in one embodiment the front face 84 of the main body 82 further can have at least one, and suitably two threaded channels 108 that allow for a screw 110 to pass through each of them respectively, the screws 110 coming into contact with the finger tabs 26 of the syringe body 24, securing the tabs 26 against the main body 82.

The main body 82 of the holder portion 78 further has a micrometer receiving aperture 112 that passes through the back face 86 of the main body 82 to the back interior end wall 98 of the interior channel 94. The micrometer receiving aperture 112 is dimensioned to allow the spindle 18 of the micrometer 10 to pass through it, and to receive at least a portion of the micrometer 10. The main body 12 of the micrometer 10 can be attached to the main body 82. In one embodiment the main body 12 of the micrometer 10 is attached to the main body 82 by a friction fit between the main body 12 of the micrometer 10 and micrometer receiving aperture 112. In another embodiment, one of the side walls 92 of the main body 82 also has a micrometer securing threaded aperture 114 that exits in the interior of the micrometer receiving aperture 112. When the micrometer 10 is received by the micrometer receiving aperture 112, a screw can be received by the micrometer securing threaded aperture 114. This screw can tightened against the micrometer 10, until the micrometer 10 is secured against the main body 82 of the holder 78.

The spindle 18 makes contact with the plunger 28, or optionally the tabbed end section 30 of the plunger 28. The spindle 18 of the micrometer 10 can be attached to either the plunger 28 or the tabbed end section 30 of the plunger 28. In one embodiment, the micrometer assisted delivery system 5 further comprises a syringe plunger holder 80 comprising a main body 116 having a front face 118, a back face 120, and a side wall 122 connecting the front 118 and back face 120. The syringe plunger holder is made of any suitable material (metal, plastic, ceramics, composites, etc.) The main body 116 further has a tabbed end section channel 124, a syringe plunger channel 126, a spindle channel 128, and a spindle securing threaded aperture 130. The syringe plunger channel 126 opens on the front face 118 of the body 166, and is dimensioned to receive the plunger 28 of a syringe 20. The tabbed end section channel 124 is dimensioned to receive the tabbed end section 30 of a syringe 20. The spindle channel 128 opens on the back face 120 of the body 116, and is dimensioned to receive the spindle 18 of a micrometer 10. The spindle securing threaded channel 130 is located on the side wall 122 of the main body 116 and exits in the interior of the spindle head channel 128. When the spindle 18 of the micrometer 10 is received by the spindle head channel 128, a screw can be received by the spindle securing threaded channel 130. This screw can be tightened against the spindle 18, until the spindle 18 is secured against the plunger holder 80.

When the syringe body 24 is secured to the holder portion 78 and the syringe plunger holder 80, and the micrometer head 10 is also secured to the holder portion 78 and the syringe plunger holder 80, the micrometer thimble 16 can then be turned to actuate the spindle 18, which in turn actuates the plunger holder 80, and in turn the plunger 28 of the syringe 20 to both dispense and aspirate liquid.

Another embodiment of the micrometer assisted delivery system 5 is shown in FIGS. 3-8. The micrometer assisted delivery system 5 comprises a micrometer head 10, a holder portion 132, a syringe 20, and a syringe plunger yoke 134.

The holder portion 132 comprises a main body 136 having a front face 138, a back face 140, a top 142, a bottom 144, side walls 146 extending from the bottom 144 to the top 142, a syringe body channel 158, a plunger yoke channel 172 and a micrometer receiving aperture 176. The holder portion 132 can be made out of any suitable material such as metal or plastic.

The syringe body channel 158 is located at the bottom 144 of the main body 136 and is dimensioned to receive the body 24 of a syringe 20. The main body 24 of the syringe 20 can be secured, attached or integral to the main body 136. In one embodiment the main body 24 of the syringe 20 is attached to the main body 136 by a friction fit between the main body 24 of the syringe 20 and the walls of the syringe body channel 158. In one embodiment the holder portion can also have a front protruding section 148 to aid in stabilizing the main body 24 of the syringe 20. The front protruding section 148 has a front face 150, a top 152, a bottom 154, and two side walls 156 extending from the bottom 154 to the top 152. The syringe body channel 158 of the main body 136 can extend through the bottom 154 of the front protruding section 148.

The plunger yoke channel 172 opens on the bottom 144 and back face 140 of the main body 136. The holder portion main body 136 can also have an access aperture 174 that is located on the side wall 146 of the holder portion main body 136 and passes through the side wall 146 to the plunger yoke channel 172.

The holder portion body 136 also has a micrometer receiving aperture 176 that passes through the front face 138 of the body 136 to the plunger yoke channel 172. The micrometer receiving aperture 176 is dimensioned to allow the spindle 18 of the micrometer 10 to pass through the aperture 176, and to receive at least a portion of the micrometer 10. The main body 12 of the micrometer 10 can be secured, attached or integral to the main body 136. In one embodiment the main body 12 of the micrometer 10 is attached to the main body 136 of the holder portion 132 by a friction fit between the main body 12 of the micrometer 10 and micrometer receiving aperture 112. In another embodiment, the holder portion main body 136 also has an adjustment channel 178 that opens on the top 142 and front face 138 of the body 136 and passes through to the plunger yoke channel 172 and to the micrometer receiving aperture 176. The body of the holder portion 136 can also have a pair of threaded channels 180 that pass through the side walls 146 of the body 136 and are aligned with each other on opposite sides of the adjustment channel 178. The micrometer head 10 is then placed in the micrometer receiving aperture 176, so that the spindle 18 extends into the plunger yoke channel 172. A screw is then threaded through the two threaded channels 180. This at least partially closes the width of the adjustment channel 178, and secures the micrometer head 10 to the holder portion body 136.

In one embodiment, the holder portion body 136 can further have a syringe tab channel 160. The tab channel 160 receives the finger tabs 26 of the syringe body 24 and a syringe holder block 162. The syringe holder block 162 has a syringe plunger channel 164. The syringe plunger holder block 162 secures the finger tabs 26 of the syringe body 24 against a side wall of the syringe tab channel 160 of the holder portion body 136. The syringe holder block 162 presses against the finger tabs 26 of the syringe body 20 by way of pressure exerted from a pair of springs 166. The springs 166 are separately received by two threaded spring channels 168 in the holder portion body 136 that extend from the back face 140 of the holder portion body to an interior of the syringe tab channel 160. The springs 166 are held in place by a pair of screws 170 that are placed in the channels 168 and tightened to position the springs 166 against the syringe holder block 162.

The syringe plunger yoke 134 of the micrometer assisted fluid delivery device comprises a body 182 having a front face 184, a back face 186, a top 188, a bottom 190, a pair of side walls 192 extending from the bottom 190 to the top 188. The syringe plunger yoke 134 is placed within the plunger yoke channel 172 of the holder portion 132. Both the plunger 28 and the spindle 18 of the micrometer 10 are attached to the plunger yoke 134. In one embodiment the spindle 18 and plunger 28 are secured by the following arrangement. The syringe plunger yoke 134 further comprises a syringe plunger channel 200, a syringe plunger tabbed end channel 202, and a spindle receiving aperture 194. In one embodiment the spindle 18 is attached to the plunger yoke 134 by a friction fit to the spindle receiving aperture 194. In another embodiment, the plunger yoke 134 has an adjustment channel 196, and a pair of threaded channels 198 that pass through the side walls 192 of the yoke body 182 and are aligned with each other on opposite sides of the adjustment channel 196. The syringe plunger channel 200 opens on the front face 184 and bottom 190 of the yoke body 182, and is dimensioned to receive the plunger 28 of a syringe 20. The syringe plunger tabbed end channel 202 opens on the bottom 190 of the yoke body 182 and is dimensioned to receive the tabbed end 30 of a syringe 20. The spindle receiving aperture 194 opens on the back face 186 of the yoke body 182, and is dimensioned to receive the spindle 18 of a micrometer head 10.

When the micrometer assisted delivery system 5 is assembled, the micrometer head 10 and the syringe 20 are attached to the holder portion 132. The syringe plunger 28 is placed within the plunger yoke channel 172 of the holder portion 132 and the syringe tabbed end 30 is received by the syringe plunger tabbed end channel 202 of the syringe plunger yoke 134. The micrometer 10 is received by the micrometer receiving aperture 176 of the holder portion 132 and the spindle receiving 194 of the syringe plunger yoke 134 receives the spindle 18 of the micrometer head 10. A screw or other fastener can then be passed through the access channel 174 of the holder body 136 and threaded through the two threaded channels of the yoke body 198, this at least partially closes the width of the adjustment channel 196, and secures the spindle 18 to the yoke body 182. When the micrometer head 10 and the syringe 20 are both connected to the holder portion 132 and the syringe plunger yoke 134, the micrometer thimble 16 can be turned to actuate the syringe plunger 28 to both dispense and aspirate liquid.

In another aspect, the invention provides a fluid delivery device that can deliver multiple individual doses of a desired amount. Each individual dose of an exact desired amount can be delivered by actuating a trigger. These embodiments of the invention are shown in FIGS. 9-15 and 21-23.

In one embodiment fluid delivery device 204 comprising a housing body 206, a pinion housing 208, a pinion 210, a detachable syringe cartridge 212 assembly, and a trigger portion 214. The parts of the fluid delivery device 204 can be made from any suitable material, including metal, plastic, ceramics or other composites.

The housing body 206 has an exterior 216 and an interior 218 with the pinion housing 208 attached on the interior 218 of the housing body 206. The housing body also has a trigger portion aperture 412 that is designed to accommodate a portion of the trigger portion 214. In one embodiment the housing body comprises a rear portion 260 and a front portion 262. The pinion housing 208 can further comprise an exterior threaded portion 264. The rear 260 and front 262 portions of the housing body 208 can also contain threaded portions in the interior 218 of the housing bodies 260, 262, so that threaded portions of the front 262 and rear 260 housing bodies engage the threaded portion 264 of the pinion housing 208, attaching the pinion housing 208 to the housing body 206. In one embodiment, the housing body 206 can also have a ring head portion 400 that is attached to the front of the housing body 206. In one embodiment the ring head portion 400 is made of a clear material and is attached in a snap fit fashion by the use of tabs 410 that interlock with the housing body 206. The ring head portion 400 can optionally have groove 416 and rib 418 portions on the interior aperture 420 of the ring head portion 400.

The pinion housing 208 has a pinion receiving aperture 220 designed to receive the pinion 210. The interior of the pinion housing 208 has a pinion guiding surface 414 that receive a portion of the pinion and allows the pinion to rotate within the pinion receiving aperture 220 of the pinion 210. The pinion 210 itself has a front section 222 having gear ridges 224, a syringe cartridge receiving aperture 226 and a rear section 228. The gear ridges 224 are equally spaced around the circumference of the front section 222.

The syringe cartridge 212 comprises a head portion 252, a syringe body 230, a main body portion 254, a plunger 234 and a needle 238. The syringe cartridge 212 is positioned within the pinion receiving aperture 220 of the pinion 210. The head portion 252 of the syringe cartridge 212 engages with a portion of the housing body 206 or, if present, the ring head portion 400. The syringe cartridge 212 can be attached to the housing body 206 or ring head portion 400 in any suitable fashion. In one embodiment, a portion of the syringe body 230 has a groove and a rib designed to mate with the groove 416 and rib 418 portions of the interior aperture 420 of the ring head portion 400. In this embodiment, when the syringe cartridge 212 is placed in the syringe cartridge receiving aperture 226 of the pinion 210 (which is itself positioned within the housing body 206) the rib of the syringe body 230 is received by the groove 416 of the ring head portion 400 and the groove of the syringe body 230 receives the rib 418 of the ring head portion 400, thus securing the syringe cartridge 212 to the housing body 206 and preventing the rotation of the syringe body 230. In other embodiments the syringe cartridge 212 can be attached to the housing body 206, or alternatively the ring head portion 400, by a friction fit or by a screw or other fastener securing the syringe cartridge 212 to the housing body 206 of ring head portion 400.

The head portion 252 of the syringe cartridge 212 contains an interior channel 266. The head portion 252 can suitably be made from a clear material, so as to visualize the plunger 234 within the interior channel 266 of the head portion 252. The head portion 252 is attached to the syringe body 230 which has an interior channel 232 that receives the plunger 234. The syringe body 230 is connected to the main body portion 254 of the syringe cartridge 212. In one embodiment the syringe body 230 is connected to the main body portion 254 by way of a rib 430 positioned on the syringe body 230 which fits into a channel 432 on the interior channel 256 of the main body portion 254. The rib 430 and channel 432 connection can be a "snap fit" designed where the rib 430 can be pushed or pulled in or out of the channel 256 when a sufficient amount of force is applied. In other embodiments, the syringe body 230 can be attached to the main body portion 254 by any other means including a friction fit connection, a connection by means of a fastener, connection by means of an adhesive, or a design whereby the syringe body 230 is integral to the main body portion 254.

The main body portion 254 of the syringe cartridge 212 also has an interior channel 256 which is aligned with the interior channel 232 of the syringe body 230 and the interior channel 266 of the head portion 252. The main body portion 254 also has a threaded portion 242 in the interior channel 256 of the portion 254. The plunger 234 is received by the interior channels 232, 256 of the syringe body 230 and the main body portion 254. The plunger 234 has a plunger tip 244, a threaded screw section 246 which engages with the threaded portion 242 of the interior channel 232 of the main body portion in a screw like fashion, and a tail section 248. The tail section 248 of the plunger 234 is received by the syringe cartridge receiving aperture 226 of the pinion 210 and engages with the rear section 228 of the pinion 210 such that when the pinion 210 is turned, the syringe plunger 234 is turned and moves forward in the syringe body 230. In one embodiment, the tail section 248 of the plunger 234 contains splines 268 and the rear section 228 of the pinion 210 contains channels 270 designed to receive the splines 268 of the tail section 248 of the plunger 234. The tail section 248 of the plunger 234 could also be operatively connected to the rear section 228 of the pinion 210 by the use of interlocking tabs, a friction fit, or by the use of a screw or other fastener securing the tail section 248 of the plunger 234 to the rear section 228 of the pinion 210.

The needle 238 of the syringe cartridge 212 is attached to the head portion 252 and is operatively connected to the interior channels 266 and 232. In one embodiment, the needle 238 can be positioned at an acute angle to the longitudinal axis 272 of the housing body 206. Suitably such an angle can be approximately 40°, though other angles can be selected.

The trigger portion 214 of the device has a button 450 and a tab section 250 which is adapted to engage with the gear ridges 224 of the pinion 210 when depressed. In one embodiment the trigger portion 214 can also have a mounting ring 452 and a cantilever spring section 454. The trigger portion 214 is attached at one end to either the housing body 206 or the pinion housing 208. In one embodiment the mounting ring 452 of the trigger portion 214 has a notch 456 which receives a rib 458 positioned on the interior 218 of the front portion 262 of housing body 206. In this embodiment, when the front portion 262 of the housing body is secured to the pinion housing 208 the trigger portion is held in place. Alternatively, the mounting ring 452 can be attached to the housing by the use of interlocking tabs, a friction fit, or by the use of a screw or other fastener securing the mounting ring 452 to the housing body 206. The mounting ring 452 may also be integral to the housing body 206 or the pinion housing 208.

The tab 250 of the trigger portion 214 is suitably flexible and has a relaxed position that causes it to bend toward the pinion 210. When the trigger 214 is depressed (shown in dashed lines in FIGS. 14 and 15), the tab 250 engages a gear ridge 224 and rotates the pinion 210 in one increment equal to the arc length of the gear ridge 224 of the pinion 210. When the pinion 210 is turned, it turns the plunger 234 and moves the plunger forward (by way of the screw like threaded engagement between the plunger 234 and the syringe main body 254) in the syringe body 230 dispending an amount of material through the needle 238. When the trigger is released, the tab 250 disengages with the gear ridge 224 and is positioned to engage with the gear ridge 244 immediately above the ridge that was just engaged when the trigger 214 was depressed previously. By this mechanism, the syringe plunger 234 dispenses a specific amount of solution with each depression of the trigger 214. Either the spacing of the gear ridges 224, or the design of the threaded section engagement of the syringe main body 254 and the plunger 234 can be designed to deliver the desired amount of solution when the trigger section is depressed.

In another aspect of the invention, the invention provides a cellular material delivery device. This aspect of the invention is best shown in FIGS. 16-20. The cellular material delivery device 280 comprises an elongated shaft 282 having a top 308, a side wall 310, a sharpened point 296 and has a diameter 284, a latitudinal axis 286 and proximal 290, medial 292 and distal 294 portions. Suitably the elongated shaft 282 can be a shaft needle, obturator, stylet, or solid wire or the like. The diameter 284 of the shaft 282 can be any desired diameter. When used to deliver hair follicle cells, one such suitable diameter 284 is less than 1 millimeter. The sharpened point 296 is located on the distal portion 294 of the shaft 282. The sharpened point 296 can be a pencil shaped point, a beveled point or a trocar shaped point having three faceted sections, or any other suitable point. It is to be understood that insertion force would likely be applied to the top 308 of the device in order to insert the device 280 into and through the skin.

The medial portion 292 of the shaft 282 has series of annular grooves 298 that run around the circumference of the shaft 282. These grooves 298 have a width 302 and a depth 306 that can be any dimensioned desired. When the device is used for delivering hair follicle cells, suitably the grooves 298 can have a depth of less than approximately 0.5 millimeters, and more suitably approximately 0.15 millimeters, and suitably a width of approximately 0.5 millimeters or less, and more suitably a width of approximately 0.2 millimeters. Many modifications in the side wall 310 of the shaft 282 can be used to accomplish the goal of subsurface delivery of cellular material. For example, square grooves, full spherical radius grooves, interrupted grooves or features that run axially or circumferentially, spirals, screw threads, or just surface roughening can be used. Even a hollow cannula could have holes or features machined into it and then have a solid wire placed within it to create a shaft 282 structure. Such grooves 298 can suitably be created using standard machining techniques on lathes or mills, EDM equipment, lasers, chemical metal removing processes or media blasting systems. These grooves 298 can also be helically orientated in one embodiment (see FIG. 20). In this embodiment the device 280 comprises helical grooves 298 which are disposed at an angle (in this embodiment 30°) with respect to the axis of the device 280. Also, the elongated shaft 282 can further have an axial channel 300 that runs along a portion of the shaft 282 and onto one of the sharpened point 296.

The structure of the cellular material delivery device 280 is intended to pick up cellular material and convey it into the skin i.e., subcutaneously, as the device 280 is inserted into the skin. Upon withdrawal of the device 280 from the skin the cellular material is deposited subepidermally and can then grow and produce, for example, a hair follicle, if hair follicle progenitor cells are used. Clearly the structure of the present invention could be used to deposit many varieties of cellular material other than follicular material intended to grow hair. One skilled in the art will also appreciate that the arrangement of radial or annular rings and/or a longitudinal groove and the number of each is a matter of design choice that will be determined in large part by the characteristics of the material to be subcutaneously deposited.

EXAMPLE 1

Use of the Micrometer Assisted Delivery Device to Deliver a Hair Follicle Cell Suspension to a Subject In this example, the embodiment of the micrometer assisted delivery device used may be any of the embodiments described above or shown in FIGS. 1-8.

Preparing the Micrometer Assisted Delivery Device

A ½ inch long 0.5 cc insulin needle is placed in the micrometer assisted delivery device holder and secured. The user should verify that the needle bevel is facing upward between the 10 o'clock to 2 o'clock positions. The user should then aspirate the required amount of solution into the micrometer assisted delivery device by turning the micrometer adjustment thimble clockwise. To push the syringe plunger forward, the user turns the micrometer adjustment thimble counterclockwise. If an air bubble is present, the user should remove by tapping the syringe body and expelling the air bubble out vertically, continue until a small volume of solution appears on the tip of the needle. Using a sterile gauze pad, the user should remove the solution from the needle tip. The micrometer head can then be locked by turning the locking collar clockwise.

Needle Insertion

The user should slide the needle superficially into the skin keeping the needle bevel side up and needle parallel to the surface of the skin. Tension in the skin may be increased by pinching the skin, spreading the skin between the user's fingers or pushing forward on the skin surface. The increased skin tension facilitates needle insertion.

The user should work the needle forward and backward along the needle track, slowly bringing the bevel of the needle closer to the surface of the skin. Approximately 4 mm-6 mm of the needle shaft should be beneath the surface of the skin. When the bevel of the needle is visible through the skin, the appropriate depth has been achieved. The user should then draw the needle back approximately 1 mm-2 mm from the distal end of the needle track.

Solution Delivery

Each increment (0.001") on the micrometer head body equals 0.25 μl of solution volume. The user should determine the number of increments to rotate the micrometer by dividing the desired volume in microliters by 0.25, e.g., 5 μl=20 increments (0.020" of micrometer head spindle travel). If required, the user should unlock the micrometer by turning the locking collar counterclockwise. The user should then inject the required amount of solution by turning the micrometer head counterclockwise, pausing for 1 second for every 2 increment increase. When finished the user may lock the micrometer head by turning the locking collar clockwise. The user should then rotate the micrometer assisted delivery device approximately 90 degrees and slowly remove the needle from the injection site.

EXAMPLE 2

Use of Fluid Delivery Device to Deliver a Hair Follicle Cell Suspension to a Subject In this example, the embodiment of the fluid delivery device used may be any of the embodiments described above or shown in FIGS. 9-15.

Preparing the Fluid Delivery Device

The needle of the syringe cartridge is placed within a cell suspension. The plunger of the syringe cartridge is rotated to pull back the syringe head and draw the cell suspension into the syringe cartridge. The syringe cartridge is placed within the housing body of the fluid delivery device. The trigger is depressed down and up until the cell suspension is visible on the needle tip.

Needle Insertion

The user should slide the needle superficially into the skin keeping the needle bevel side up and needle parallel to the surface of the skin. Tension in the skin may be increased by pinching the skin, spreading the skin between the user's fingers or pushing forward on the skin surface. The increased skin tension facilitates needle insertion.

The user should work the needle forward and backward along the needle track, slowly bringing the bevel of the needle closer to the surface of the skin. Approximately 4 mm-6 mm of the needle shaft should be beneath the surface of the skin. When the bevel of the needle is visible through the skin, the appropriate depth has been achieved. The user should then draw the needle back approximately 1 mm-2 mm from the distal end of the needle track.

Solution Delivery

The user should then inject the predetermined amount of solution by pressing the trigger portion on the device. The user should then rotate the micrometer assisted delivery device approximately 90 degrees and slowly remove the needle from the injection site.

EXAMPLE 3

Use of the Cellular Material Delivery Device

In this example, the embodiment of the cellular material device used may be any of the embodiments described above or shown in FIGS. 16-20.

Trichogenic epithelial and dermal cells were aggregated and placed in a suspension on the back of a nu/nu mouse. Using the cellular material device, the skin of the mouse was pierced and the device was inserted into the mouse, the annular grooves picking up the suspension from the surface and conveying the material beneath the surface of the skin of the mouse. The injections were repeated by 20× penetrations of the skin through the cell suspension drop. After 10 days of incubation hair follicle formation was seen within the dermis. This experiment was repeated, with the same success, on two further occasions using the same needle configuration.

While the present invention has now been described and exemplified with some specificity, those skilled in the art will appreciate the various modifications, including variations, additions, and omissions, that may be made in what has been described. Accordingly, it is intended that these modifications also be encompassed by the present invention and that the scope of the present invention be limited solely by the broadest interpretation that lawfully can be accorded the appended claims.

The invention claimed is:

1. A housing body for a fluid delivery device comprising:
   an exterior and an interior and a cartridge aperture;
   a pinion housing attached to the interior of the housing body, the pinion housing having a pinion receiving aperture;
   a pinion which is received by the pinion receiving aperture, and attached to the pinion housing within the pinion receiving aperture, the pinion comprising a front section having gear ridges, a cartridge receiving aperture, and a rear section;
   and a trigger portion having a tab section which is adapted to engage with the gear ridges of the pinion when depressed, and wherein the pinion rotates within the pinion receiving aperture when the trigger portion is depressed.

2. The housing body of claim 1 wherein the housing body comprises a rear portion and a front portion.

3. The housing body of claim 2 wherein the pinion housing further comprises an exterior threaded portion and the rear and front portion of the housing body contain threaded portions in the interior of the housing bodies, wherein the threaded portions of the front and rear housing bodies engage the threaded portion of the pinion housing.

4. A method of delivering cellular material comprising injecting the cellular material to a subject using a fluid delivery device, wherein the cellular material comprises cells that retain their inherent morphologic characteristics upon injection, and
   wherein the fluid delivery device comprises
      a housing body and a detachable cartridge,
      wherein the housing body comprises an exterior and an interior and a cartridge aperture;
      a pinion housing attached to the interior of the housing body, the pinion housing having a pinion receiving aperture;
      a pinion which is received by the pinion receiving aperture, and attached to the pinion housing within the pinion receiving aperture, the pinion comprising a front section having gear ridges, a cartridge receiving aperture, and a rear section;
      and a trigger portion having a tab section which is adapted to engage with the gear ridges of the pinion when depressed, and wherein the pinion rotates within the pinion receiving aperture when the trigger portion is depressed, and
      wherein the detatchable cartridge comprises a head portion, a cartridge body, a main body portion, a plunger and a needle;
      wherein the head portion engages the housing body and is attached to the cartridge body;
      wherein the cartridge body has an interior channel; the main body portion has an interior channel, the main body portion being attached to the cartridge body and the interior channel of the main body portion having a threaded portion;

wherein the plunger is received by the interior channel of the cartridge body and the main body portion, the plunger having a plunger tip, a threaded screw section which engages with the threaded portion of the interior channel of the main body portion, and a tail section which is received by the cartridge receiving aperture of the pinion and which engages with the rear section of the pinion; and wherein the needle is attached to the head portion of the cartridge and is operatively connected to the interior channel of the cartridge body.

5. The method of claim 4, wherein the cellular material further comprises a suspension media.

6. The method of claim 4, wherein the cellular material is delivered to a subject in an amount effective to treat a disease or a physical condition which afflicts the subject.

7. The method of claim 6, wherein the disease or condition is hair loss.

8. The method of claim 6, wherein the disease or physical condition is selected from the group consisting of hair loss, psoriasis, diabetes, rhytids, skin atrophy, tooth loss, skin ulcers, bed sores, diabetic foot ulcers, burn wounds, microbial infections, surgical scars, acne, chicken pox and combinations thereof.

9. The method of claim 4, wherein the cells comprise follicular progenitor cells.

10. The method of claim 9, wherein the follicular progenitor cells are autologous.

11. The method of claim 10, wherein the cells comprise dermal cells.

12. The method of claim 10, wherein the cells comprise epidermal cells.

13. The method of claim 4, wherein the cells are delivered to the skin's sub-epidermal layer, papillary dermal layer or upper reticular dermal layer.

14. The method of claim 4 wherein the cells are delivered to the skin of the subject.

15. A method of delivering a material into a subject's skin using a fluid delivery device, wherein the fluid delivery device comprises a housing body and a detachable cartridge, wherein the housing body comprises an exterior and an interior and a cartridge aperture;

a pinion housing attached to the interior of the housing body, the pinion housing having a pinion receiving aperture;

a pinion which is received by the pinion receiving aperture, and attached to the pinion housing within the pinion receiving aperture, the pinion comprising a front section having gear ridges, a cartridge receiving aperture, and a rear section;

and a trigger portion having a tab section which is adapted to engage with the gear ridges of the pinion when depressed, and wherein the pinion rotates within the pinion receiving aperture when the trigger portion is depressed, and wherein the detatchable cartridge comprises a head portion, a cartridge body, a main body portion, a plunger and a needle;

wherein the head portion engages the housing body and is attached to the cartridge body;

wherein the cartridge body has an interior channel; the main body portion has an interior channel, the main body portion being attached to the cartridge body and the interior channel of the main body portion having a threaded portion;

wherein the plunger is received by the interior channel of the cartridge body and the main body portion, the plunger having a plunger tip, a threaded screw section which engages with the threaded portion of the interior channel of the main body portion, and a tail section which is received by the cartridge receiving aperture of the pinion and which engages with the rear section of the pinion; and wherein the needle is attached to the head portion of the cartridge and is operatively connected to the interior channel of the cartridge body, the method comprising the steps of:
 i) loading the cartridge into the housing body of the fluid delivery device, wherein the cartridge body is filled with the material;
 ii) inserting the needle of the fluid delivery device into the skin at an angle about parallel to skin until a desired depth has been reached;
 iii) injecting an amount of the material by depressing the trigger portion of the fluid delivery device;
 iv) rotating the fluid delivery device approximately 45 to 90 degrees; and
 v) removing the needle from the injection site.

16. The method of claim 15, wherein in step ii), four to six millimeters of the needle is below the skin surface.

17. The method of claim 16, further comprising, between steps ii) and iii), drawing 1 to 2 mm of the needle out of the skin.

18. The method of claim 15, wherein the material is selected from the group consisting of botox, collagen, hyaluronic acid, antibiotics, anti-inflammatory drugs, steroids and combinations thereof.

19. The method of claim 15, wherein the material is a cellular material comprising cells.

20. The method of claim 19, wherein the cells are selected from the group consisting of dermal cells, epidermal cells, epidermal stem cells, basal cells, keratinocytes, melanocytes, trichogenic dermal cells, fibroblasts, follicular progenitor cells, pancreatic islet cells, adipose cells, dental epithelial cells, dental dermal cells and combinations thereof.

21. The method of claim 19, wherein the cells retain their inherent morphologic characteristics upon injection.

22. The method of claim 15, wherein in step iii) further comprises:
 engaging one gear ridge with the tab section of the trigger portion,
 rotating the pinion one increment, wherein one increment is equal to the arc length of the gear ridge of the pinion, and
 turning the plunger to move the plunger forward in the cartridge body and thereby inject the amount of the material.

23. A fluid delivery device comprising a housing body and a detachable cartridge, wherein the housing body comprises an exterior and an interior and a cartridge aperture;

a pinion housing attached to the interior of the housing body, the pinion housing having a pinion receiving aperture;

a pinion which is received by the pinion receiving aperture, and attached to the pinion housing within the pinion receiving aperture, the pinion comprising a front section having gear ridges, a cartridge receiving aperture, and a rear section;

and a trigger portion having a tab section which is adapted to engage with the gear ridges of the pinion when depressed, and wherein the pinion rotates within the pinion receiving aperture when the trigger portion is depressed, and wherein the detatchable cartridge comprises a head portion, a cartridge body, a main body portion, a plunger and a needle;

the head portion engages the housing body and is attached to the cartridge body;

the cartridge body has an interior channel; the main body portion has an interior channel, the main body portion being attached to the cartridge body and the interior channel of the main body portion having a threaded portion;

the plunger is received by the interior channel of the cartridge body and the main body portion, the plunger having a plunger tip, a threaded screw section which engages with the threaded portion of the interior channel of the main body portion, and a tail section which is received by the cartridge receiving aperture of the pinion and which engages with the rear section of the pinion; and the needle is attached to the head portion of the cartridge and is operatively connected to the interior channel of the cartridge body.

24. The cartridge of claim 23 wherein the head portion of the cartridge is made from a clear material.

25. The cartridge of claim 23 wherein the tail section of the plunger is splined.

26. The fluid delivery device of claim 23 wherein the housing body has a longitudinal axis and wherein the needle is at an acute angle to the longitudinal axis of the housing body.

27. The fluid delivery device of claim 26 wherein the needle is at an approximately 40° angle to the longitudinal axis of the housing body.

28. The fluid delivery device of claim 23, wherein the housing body comprises a rear portion and a front portion.

29. The fluid delivery device of claim 28, wherein the pinion housing further comprises an exterior threaded portion and the rear and front portion of the housing body contain threaded portions in the interior of the housing bodies, wherein the threaded portions of the front and rear housing bodies engage the threaded portion of the pinion housing.

30. The fluid delivery device of claim 23 wherein the head portion of the cartridge is made from a clear material.

31. The fluid delivery device of claim 23 wherein the tail section of the plunger is splined and the rear section of the pinion contains channels designed to receive the splines of the tail section of the plunger.

* * * * *

UNITED STATES PATENT AND TRADEMARK OFFICE
CERTIFICATE OF CORRECTION

PATENT NO. : 7,780,635 B2  Page 1 of 1
APPLICATION NO. : 11/672675
DATED : August 24, 2010
INVENTOR(S) : Terrell Pruitt et al.

It is certified that error appears in the above-identified patent and that said Letters Patent is hereby corrected as shown below:

Claim 13, column 17, line 36, replace "claim 4" with --claim 12--.

Signed and Sealed this
Twenty-fourth Day of May, 2011

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,780,635 B2 | Page 1 of 1 |
| APPLICATION NO. | : 11/672675 | |
| DATED | : August 24, 2010 | |
| INVENTOR(S) | : Terrell A Pruitt et al. | |

It is certified that error appears in the above-identified patent and that said Letters Patent is hereby corrected as shown below:

Specification, column 4, line 48, replace "cite" with --site--.

Claim 24, column 20, lines 1 through 2, cancel claim 24.

Claim 25, column 20, lines 3 through 4, replace "The cartridge" with --The fluid delivery device--.

Signed and Sealed this
Second Day of October, 2012

David J. Kappos
*Director of the United States Patent and Trademark Office*